US009399681B2

(12) United States Patent
Anderl et al.

(10) Patent No.: US 9,399,681 B2
(45) Date of Patent: Jul. 26, 2016

(54) AMATOXIN-CONJUGATES WITH IMPROVED LINKERS

(75) Inventors: Jan Anderl, Modautal (DE); Werner Simon, Hueffelsheim (DE); Christoph Mueller, Birkenau (DE)

(73) Assignee: Heldelberg Pharma GmbH, Ladenburg (DE)

( * ) Notice: Subject to any disclaimer, the term of this patent is extended or adjusted under 35 U.S.C. 154(b) by 0 days.

(21) Appl. No.: 13/876,829

(22) PCT Filed: Sep. 29, 2011

(86) PCT No.: PCT/EP2011/004875
§ 371 (c)(1),
(2), (4) Date: Jun. 17, 2013

(87) PCT Pub. No.: WO2012/041504
PCT Pub. Date: Apr. 5, 2012

(65) Prior Publication Data

US 2013/0259880 A1 Oct. 3, 2013

(30) Foreign Application Priority Data

Sep. 30, 2010 (EP) .................................... 10012573

(51) Int. Cl.
*A61K 47/48* (2006.01)
*C07K 16/30* (2006.01)

(52) U.S. Cl.
CPC ........... *C07K 16/30* (2013.01); *A61K 47/48415* (2013.01); *A61K 47/48561* (2013.01); *A61K 47/48569* (2013.01); *A61K 47/48584* (2013.01)

(58) Field of Classification Search
USPC ............................. 424/179.1; 530/321, 391.1
See application file for complete search history.

(56) References Cited

U.S. PATENT DOCUMENTS

| | | | | |
|---|---|---|---|---|
| 5,378,688 | A | 1/1995 | Nett et al. | |
| 2012/0100161 | A1* | 4/2012 | Faulstich et al. | 424/183.1 |

FOREIGN PATENT DOCUMENTS

| | | | | | |
|---|---|---|---|---|---|
| EP | 1661584 | A1 | 5/2006 | | |
| EP | 1 859811 | A1 | * 11/2007 | | A61K 47/48 |
| WO | WO 2007/121326 | A2 | 10/2007 | | |
| WO | WO 2010/115629 | | * 10/2010 | | A61K 47/48 |
| WO | WO 2010/115629 | A2 | 10/2010 | | |
| WO | WO 2010/115630 | A1 | 10/2010 | | |
| WO | WO 2014/043403 | A1 | 3/2014 | | |

OTHER PUBLICATIONS

Faulstich and Fiume (Methods in Enzymology, 1985, 112: 225-237).*

Barbanti-Brodano, et al., "Selective killing of macrophages by amanitin-albumin conjugates," Nature New Biology, Jun. 27, 1973; vol. 243(130): pp. 281-283.

Baumann, et al., "Identification of structural features involved in binding of alpha-amanitin to a monoclonal antibody," Biochemistry, Apr. 20, 1993; vol. 32(15): pp. 4043-4050.

Bonetti, et al., "Increased penetration of amanitine into hepatocytes when conjugated with albumin," Arch Toxicol., Jan. 30, 1976; vol. 35(1): pp. 69-73.

Cessi,et al., "Increased toxicity of beta-amanitin when bound to a protein," Toxicon. May 1969; vol. 6(4): pp. 309-310.

Chen, et al., "Polyclonal amanitin-specific antibodies: production and cytoprotective properties in vitro," Biochem Pharmacol., Jul. 20, 1993; vol. 46(2): pp. 327-329.

Davis, et al., "A conjugate of alpha-amanitin and monoclonal immunoglobulin G to Thy 1.2 antigen is selectively toxic to T lymphoma cells," Science, Sep. 18, 1981; vol. 213(4514): pp. 1385-1388.

Derenzini, et al., "Pathogenesis of liver necrosis produced by amanitin-albumin conjugates," Lab Invest., Aug. 1973; vol. 29(2): pp. 150-158.

Faulstich, et al., "A radioimmunoassay for amanitin," FEBS Letters, Aug. 15, 1975; vol. 56(2): pp. 312-315.

Faulstich, et al., "Ether derivatives of alpha-amanitin. Introduction of spacer moieties, lipophilic residues, and radioactive labels," Biochemistry, Oct 27, 1981; vol. 20(22): pp. 6498-6504.

Fiume, L., "Penetration of a beta-amanitin-rabbit-albumin conjugate into hepatic parenchymal cells," Lancet, Oct. 18, 1969; vol. 2(7625): pp. 853-854.

Fiume, et al., "Facilitated penetration of amanitin-albumin conjugates into hepatocytes after coupling with fluorescein," Nat New Biol., Apr. 14, 1971; vol. 230(15): pp. 219-220.

Baumann, et al., "A Beta-turn in Alpha-amanitin is the most important structural feature for binding to RNA polymerase II and three monoclonal antibodies," Protein Science : A Publication of the Protein Society (1994); vol. 3, pp. 750-756.

Bermbach U. and Faulstich H., "Epidermal Growth Factor Labeled Beta-Amanitin-Poly-L-ornithine: Preparation and Evidence for Specific Cytotoxicity,"Biochemistry. (1990); vol. 29: pp. 6839-6845.

Faulstich et al., "Amanita Toxins Bound to Biopolymers," Peptides, Proc. Eur. Pept. Symp., 13th, Apr. 28-May 3, 1974, Wiley, New York, (1975); pp. 333-338.

Guo et al., "[Culture conditions and analysis of amanitins on Amanita spissa]," J. Acta Microbiologica Sinica (2006); vol. 46(3): pp. 373-378.

Morris, P.W. & Venton, D.L., "Regiospecific amine substitution into alpha-amanitin with retention of inhibitory properties against eukaryotic class II RNA polymerase," Int. J. Peptide Protein Res. (1983); vol. 21 419-430 Int. J. Pept. Protein Res. (1983); vol. 21: pp. 419-430.

Muraoka, S. and Shinozawa, T., "Effective Production of Amanitins by Two-Step Cultivation of the Basidiomycete, Galerina Fasciculata GF-060," J. Biosci. Bioeng., (2000); vol. 89(1): pp. 73-76.

(Continued)

*Primary Examiner* — Yan Xiao
(74) *Attorney, Agent, or Firm* — Arnold & Porter LLP; Todd A. Lorenz

(57) ABSTRACT

The invention relates to tumor therapy. In one aspect, the present invention relates to conjugates of an amatoxin and a target-binding moiety, e.g. an antibody, connected by a linker comprising a urea moiety, which are useful in the treatment of cancer. In a further aspect the invention relates to pharmaceutical compositions comprising such conjugates.

16 Claims, 6 Drawing Sheets

(56) References Cited

OTHER PUBLICATIONS

Wieland, T. and Faulstich, H., "Amatoxins, Phallotoxins, Phallolysin, and Antamanide: The Biologically Active Components of Poisonous Amanita Mushrooms," Crit. Rev. Biochem. (1978): vol. 5(3); pp. 185-260.

Wieland, Th., et al., "Die absoluten Konfigurationen der in den Phytotoxinen enthaltenen γ-Hydroxyaminosauren and der γ-Hydroxynorvaline." Liebigs Ann. Chem. (1968); vol. 717: pp. 205-214.

Zanotti et al., "Synthesis of analogues of annaninamide, an amatoxin from the white Amanita virosa mushroom," Int. J. Peptide Protein Res. (1987); vol. 30: pp. 450-459.

Zanotti et al., "Structure-toxicity relationships in the amatoxin series. Synthesis of S-deoxy[γ(R)-hydroxy-lle3]-amaninamide, its crystal and molecular structure and inhibitory efficiency," Int. J. Pept. Protein Res. (1989); vol. 34: pp. 222-228.

Zanotti et al., "Structure-toxicity relationships in the amatoxin series. Structural variations of side chain 3 and inhibition of RNA polymerase II," Int. J. Pept. Protein Res. (1992); vol. 40: pp. 551-558.

Zhang et al., "Production and characterization of Amanitin toxins from a pure culture of Amanita exitialis," FEMS Microbiol Lett. (2005); vol. 252: pp. 223-228.

Zhelev at al., "Preparation of a β-Amanitin-Concanavalin a Conjugate of Low Toxicity," Toxicon (1987); vol. 25(9): pp. 981-987.

* cited by examiner

| | $R_1$ | $R_2$ | $R_3$ | $R_4$ |
|---|---|---|---|---|
| α-amanitin | OH | OH | $NH_2$ | OH |
| β-amanitin | OH | OH | OH | OH |
| γ-amanitin | H | OH | $NH_2$ | OH |
| ε-amanitin | H | OH | OH | OH |
| amanin | OH | OH | OH | H |
| amaninamide | OH | OH | $NH_2$ | H |
| amanullin | H | H | $NH_2$ | OH |
| amanullinic acid | H | H | OH | OH |

AMATOXIN-CONJUGATES WITH IMPROVED LINKERS

FIELD OF THE INVENTION

The invention relates to tumour therapy. In one aspect, the present invention relates to conjugates of an amatoxin and a target-binding moiety, e.g. an antibody, connected by a linker comprising a urea moiety, which are useful in the treatment of cancer. In a further aspect the invention relates to pharmaceutical compositions comprising such conjugates.

BACKGROUND OF THE INVENTION

Amatoxins are cyclic peptides composed of 8 amino acids. They can be isolated from *Amanita phalloides* mushrooms or prepared synthetically. Amatoxins specifically inhibit the DNA-dependent RNA polymerase II of mammalian cells, and thereby also the transcription and protein biosynthesis of the affected cells. Inhibition of transcription in a cell causes stop of growth and proliferation. Though not covalently bound, the complex between amanitin and RNA-polymerase II is very tight ($K_D$=3 nM). Dissociation of amanitin from the enzyme is a very slow process, thus making recovery of an affected cell unlikely. When the inhibition of transcription lasts too long, the cell will undergo programmed cell death (apoptosis).

The use of amatoxins as cytotoxic moieties for tumour therapy had already been explored in 1981 by coupling an anti-Thy 1.2 antibody to α-amanitin using a linker attached to the indole ring of Trp (amino acid 4; see FIG. 1) via diazotation (Davis & Preston, Science 1981, 213, 1385-1388).

Patent application EP 1 859 811 A1 (published Nov. 28, 2007) described conjugates, in which the γ C-atom of amatoxin amino acid 1 of β-amanitin was directly coupled, i.e. without a linker structure, to albumin or to monoclonal antibody HEA125, OKT3, or PA-1. Furthermore, the inhibitory effect of these conjugates on the proliferation of breast cancer cells (MCF-7), Burkitt's lymphoma cells (Raji), and T-lymphoma cells (Jurkat) was shown. The use of linkers was suggested, including linkers comprising elements such as amide, ester, ether, thioether, disulfide, urea, thiourea, hydrocarbon moieties and the like, but no such constructs were actually shown, and no more details, such as attachment sites on the Amatoxins, were provided.

It is known that amatoxins are relatively non-toxic when coupled to large biomolecule carriers, such as antibody molecules, and that they exert their cytotoxic activity only after the biomolecule carrier is cleaved off. In light of the toxicity of amatoxins, particularly for liver cells, it is of outmost importance that amatoxin conjugates for targeted tumour therapy remain highly stable after administration in plasma, and that the release of the amatoxin occurs after internalization in the target cells. In this context, minor improvements of the conjugate stability may have drastic consequences for the therapeutic window and the safety of the amatoxin conjugates for therapeutic approaches.

OBJECT OF THE INVENTION

Thus, there was a high need in the prior art for target-binding moiety amatoxin conjugates that are stable in plasma, so that harmful side effects to non-target cells are minimized.

SUMMARY OF THE INVENTION

In a first aspect the present invention relates to a conjugate comprising a target-binding moiety linked via a linker L to an amatoxin, wherein the linker L is connected to the amatoxin via (i) the γ C-atom of amatoxin amino acid 1, particularly via an amide linkage;

(ii) an oxygen atom bound to the δ C-atom of amatoxin amino acid 3, particularly via an ester linkage, an ether linkage or a urethane linkage; or (iii) the 6' C-atom of amatoxin amino acid 4, particularly via an oxygen atom bound to the 6' C-atom of amatoxin amino acid 4;

in each case wherein the linker L is connected to the target-binding moiety via a urea moiety.

In a second aspect the present invention relates to a pharmaceutical composition comprising the conjugate according to the present invention.

In another aspect, the present invention relates to an amatoxin-conjugation molecule comprising a linker L connected to an amatoxin via (i) the γ C-atom of amatoxin amino acid 1, particularly via an amide linkage;

(ii) an oxygen atom bound to the δ C-atom of amatoxin amino acid 3, particularly via an ester linkage, an ether linkage or a urethane linkage; or (iii) the 6' C-atom of amatoxin amino acid 4, particularly via an oxygen atom bound to the 6' C-atom of amatoxin amino acid 4;

in each case wherein the linker L comprises a carbamic acid derivative —NH—C(O)—X, wherein X is a leaving group that can be replaced by a primary amine of a target-binding moiety.

In yet another aspect, the present invention relates to a method for synthesizing a conjugate of the present invention, comprising the step of reacting an amatoxin-conjugation molecule of the present invention with a target-binding moiety comprising a primary amino group.

DETAILED DESCRIPTION OF THE INVENTION

Figure 1:
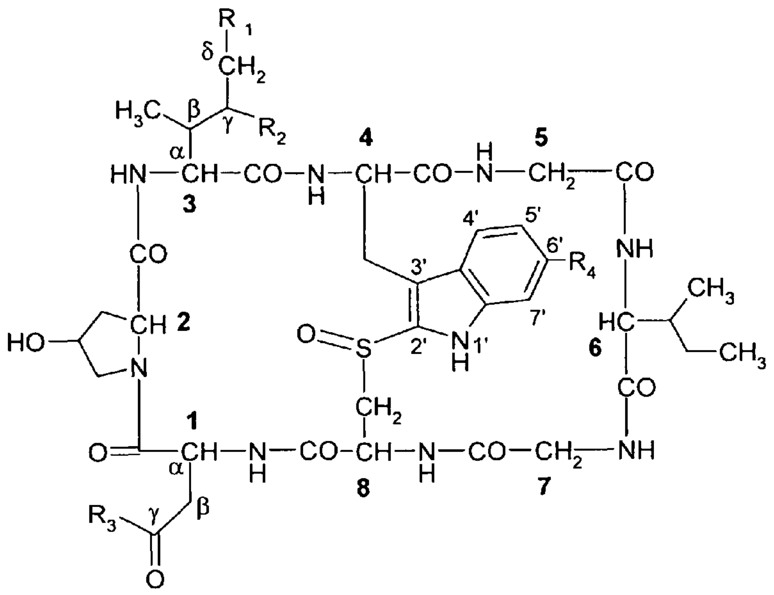
FIG. 1 shows the structural formulae of different amatoxins. The numbers in bold type (1 to 8) designate the standard numbering of the eight amino acids forming the amatoxin. The standard designations of the atoms in amino acids 1, 3 and 4 are also shown (Greek letters α to γ, Greek letters α to δ, and numbers from 1' to 7', respectively).
Figure 2:
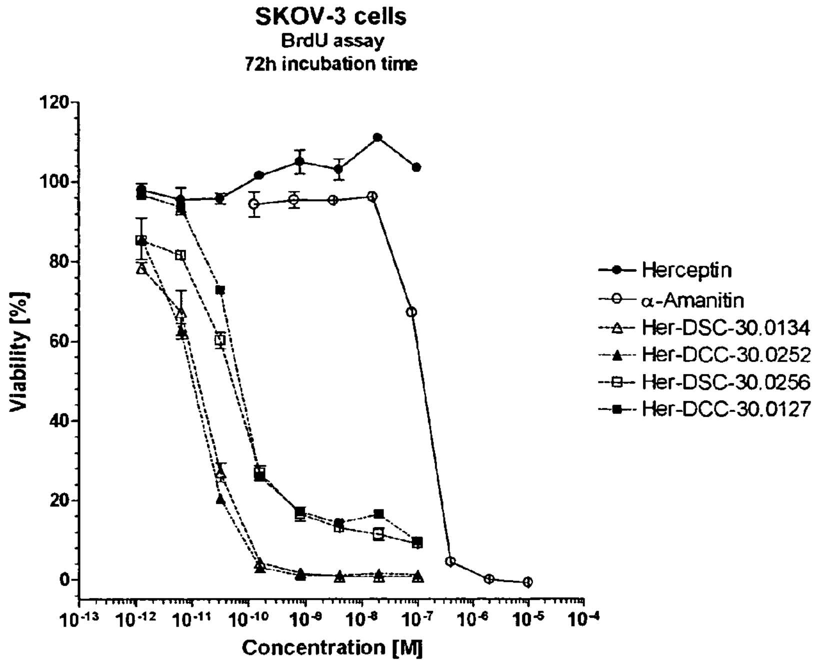
FIG. 2 shows the cytotoxic activity of different amanitin herceptin conjugates using different linker moieties on SKOV-3 cells in a BrdU assay after incubation for 72 h.
Figure 3:
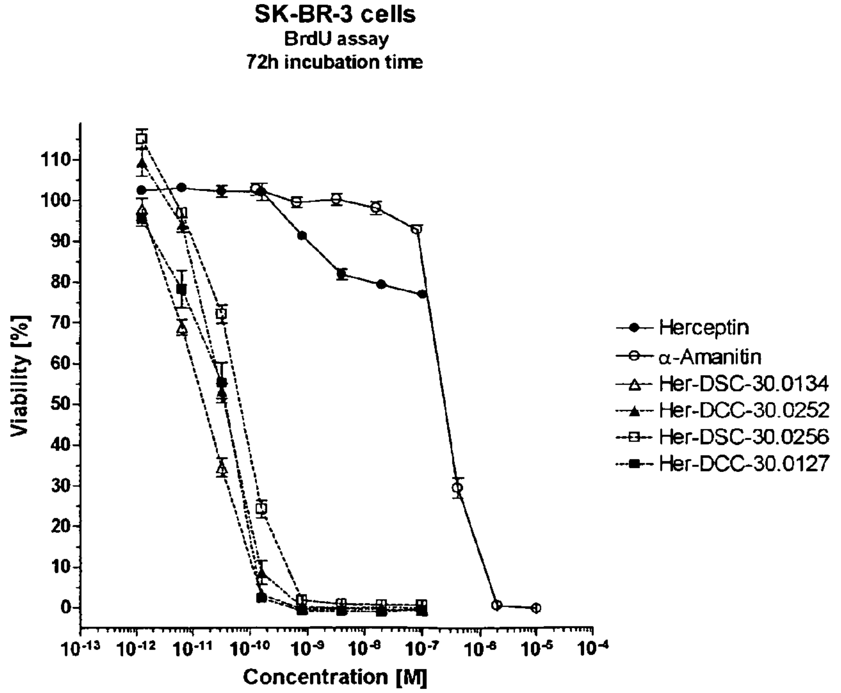
FIG. 3 shows the cytotoxic activity of different amanitin herceptin conjugates using different linker moieties on SK-BR-3 cells in a BrdU assay after incubation for 72 h.
Figure 4:
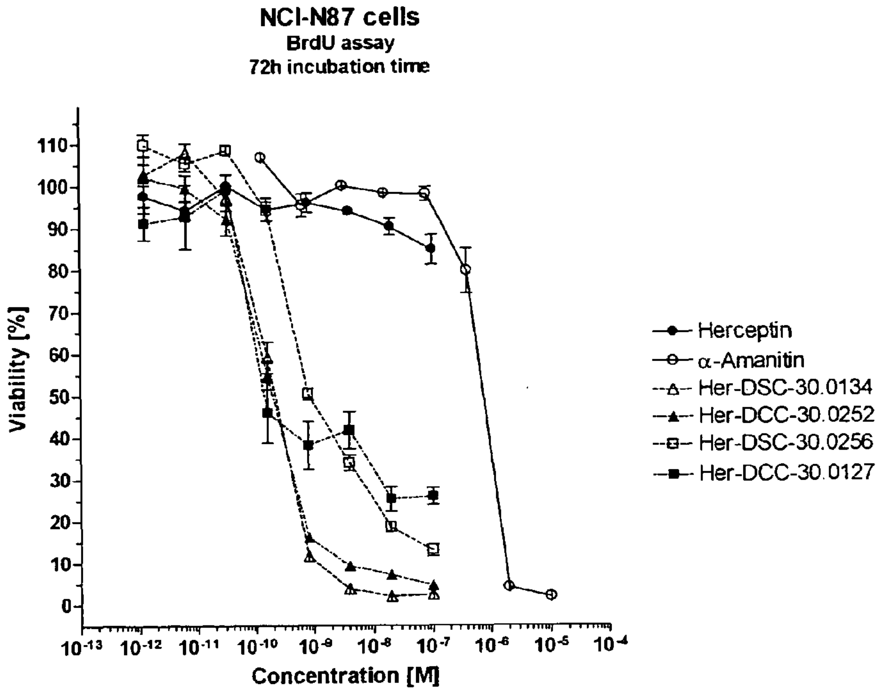
FIG. 4 shows the cytotoxic activity of different amanitin herceptin conjugates using different linker moieties on NCI-N87 cells in a BrdU assay after incubation for 72 h.
Figure 5:
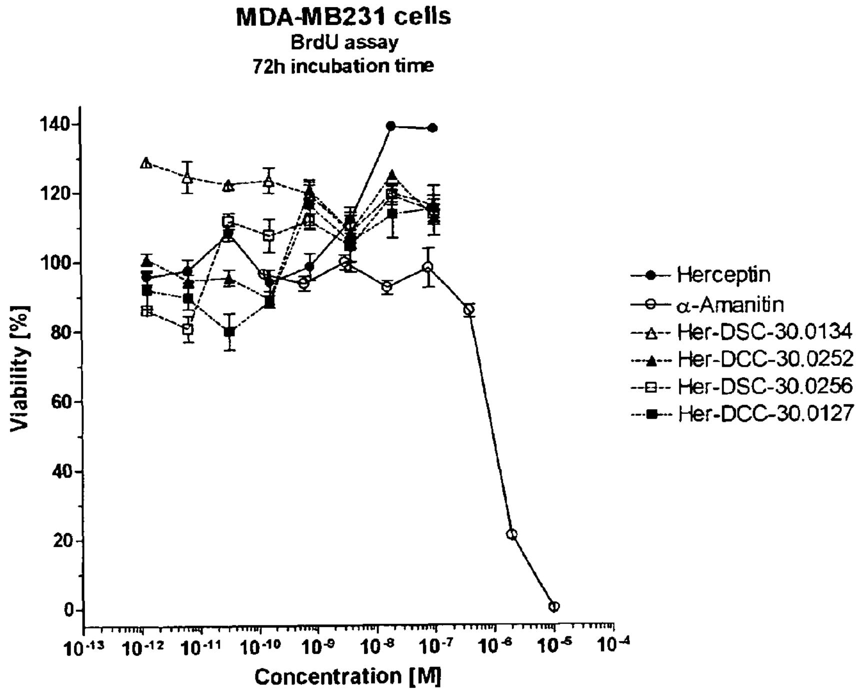
FIG. 5 shows the cytotoxic activity of different amanitin herceptin conjugates using different linker moieties on MDA-MB231 cells in a BrdU assay after incubation for 72 h.

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety to the extent possible under the respective patent law. Nothing herein is to be construed as an admission that the invention is not entitled to antedate such disclosure by virtue of prior invention.

The present invention will now be further described. In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In a first aspect the present invention relates to a conjugate comprising a target-binding moiety linked via a linker L to an amatoxin, wherein the linker L is connected to the amatoxin via (iv) the γ C-atom of amatoxin amino acid 1, particularly via an amide linkage;

(v) an oxygen atom bound to the δ C-atom of amatoxin amino acid 3, particularly via an ester linkage, an ether linkage or a urethane linkage; or (vi) the 6' C-atom of amatoxin amino acid 4, particularly via an oxygen atom bound to the 6' C-atom of amatoxin amino acid 4;

in each case wherein the linker L is connected to the target-binding moiety via a urea moiety.

In the context of the present invention, the term "conjugate" refers to a molecule comprising at least two different molecules linked by a covalent bond.

The term "target-binding moiety", as used herein, refers to any molecule or part of a molecule that can specifically bind to a target molecule or target epitope. Preferred target-binding moieties in the context of the present application are (i) antibodies or antigen-binding fragments thereof; (ii) antibody-like proteins; and (iii) nucleic acid aptamers. "Target-binding moieties" suitable for use in the present invention typically have a molecular mass of 40 000 Da (40 kDa) or more.

As used herein, a first compound (e.g. an antibody) is considered to "specifically bind" to a second compound (e.g. an antigen, such as a target protein), if it has a dissociation constant $K_D$ to said second compound of 100 μM or less, preferably 50 μM or less, preferably 30 μM or less, preferably 20 μM or less, preferably 10 μM or less, preferably 5 μM or less, more preferably 1 μM or less, more preferably 900 nM or less, more preferably 800 nM or less, more preferably 700 nM or less, more preferably 600 nM or less, more preferably 500 nM or less, more preferably 400 nM or less, more preferably 300 nM or less, more preferably 200 nM or less, even more preferably 100 nM or less, even more preferably 90 nM or less, even more preferably 80 nM or less, even more preferably 70 nM or less, even more preferably 60 nM or less, even more preferably 50 nM or less, even more preferably 40 nM or less, even more preferably 30 nM or less, even more preferably 20 nM or less, and even more preferably 10 nM or less.

In the context of the present application the terms "target molecule" and "target epitope", respectively, refers to an antigen and an epitope of an antigen, respectively, that is specifically bound by a target-binding moiety. Preferably the target molecule is a tumour-associated antigen, in particular an antigen or an epitope which is present on the surface of one or more tumour cell types in an increased concentration and/or in a different steric configuration as compared to the surface of non-tumour cells Preferably, said antigen or epitope is present on the surface of one or more tumour cell types, but not on the surface of non-tumour cells. In particular embodiments, the target-binding moiety specifically binds to an epitope of HER-2/neu or epithelial cell adhesion molecule (EpCAM). In other embodiments, said antigen or epitope is preferentially expressed on cells involved in autoimmune diseases. In particular such embodiments, the target-binding moiety specifically binds to an epitope of the IL-6 receptor (IL-6R).

The term "antibody or antigen binding fragment thereof", as used herein, refers to immunoglobulin molecules and immunologically active portions of immunoglobulin molecules, i.e. molecules that contain an antigen binding site that immunospecifically binds an antigen. Also comprised are immunoglobulin-like proteins that are selected through techniques including, for example, phage display to specifically bind to a target molecule, e.g. to the target protein Her-2/neu or EpCAM. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. "Antibodies and antigen-binding fragments thereof" suitable for use in the present invention include, but are not limited to, polyclonal, monoclonal, monovalent, bispecific, heteroconjugate, multispecific, human, humanized (in particular CDR-grafted), deimmunized, or chimeric antibodies, single chain antibodies (e.g. scFv), Fab fragments, $F(ab')_2$ fragments, fragments produced by a Fab expression library, diabodies or tetrabodies (Holliger P. et al., 1993), nanobodies, anti-idiotypic (anti-Id) antibodies (including, e.g., anti-Id antibodies to antibodies of the invention), and epitope-binding fragments of any of the above.

In some embodiments the antigen-binding fragments are human antigen-binding antibody fragments of the present invention and include, but are not limited to, Fab, Fab' and $F(ab')_2$, Fd, single-chain Fvs (scFv), single-chain antibodies, disulfide-linked Fvs (dsFv) and fragments comprising either a VL or VH domain. Antigen-binding antibody fragments, including single-chain antibodies, may comprise the variable domain(s) alone or in combination with the entirety or a portion of the following: hinge region, CL, CH1, CH2, and CH3 domains. Also included in the invention are antigen-binding fragments also comprising any combination of variable domain(s) with a hinge region, CL, CH1, CH2, and CH3 domains.

Antibodies usable in the invention may be from any animal origin including birds and mammals. Preferably, the antibodies are from human, rodent (e.g. mouse, rat, guinea pig, or rabbit), chicken, pig, sheep, goat, camel, cow, horse, donkey, cat, or dog origin. It is particularly preferred that the antibodies are of human or murine origin. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins, as described for example in U.S. Pat. No. 5,939,598 by Kucherlapati & Jakobovits.

The term "antibody-like protein" refers to a protein that has been engineered (e.g. by mutagenesis of loops) to specifically bind to a target molecule. Typically, such an antibody-like protein comprises at least one variable peptide loop attached at both ends to a protein scaffold. This double structural constraint greatly increases the binding affinity of the antibody-like protein to levels comparable to that of an antibody. The length of the variable peptide loop typically consists of 10 to 20 amino acids. The scaffold protein may be any protein having good solubility properties. Preferably, the scaffold protein is a small globular protein. Antibody-like proteins include without limitation affibodies, anticalins, and designed ankyrin repeat proteins (for review see: Binz et al. 2005). Antibody-like proteins can be derived from large libraries of mutants, e.g. be panned from large phage display libraries and can be isolated in analogy to regular antibodies. Also, antibody-like binding proteins can be obtained by combinatorial mutagenesis of surface-exposed residues in globular proteins.

The term "nucleic acid aptamer" refers to a nucleic acid molecule that has been engineered through repeated rounds of in vitro selection or SELEX (systematic evolution of ligands by exponential enrichment) to bind to a target molecule (for a review see: Brody and Gold, 2000). The nucleic acid aptamer may be a DNA or RNA molecule. The aptamers may contain modifications, e.g. modified nucleotides such as 2'-fluorine-substituted pyrimidines.

As used herein, a "chemical derivative" (or short: a "derivative") of a compound refers to a species having a chemical structure that is similar to the compound, yet containing at least one chemical group not present in the compound and/or deficient of at least one chemical group that is present in the compound. The compound to which the derivative is compared is known as the "parent" compound. Typically, a "derivative" may be produced from the parent compound in one or more chemical reaction steps.

As used herein, an "analogue" of a compound is structurally related but not identical to the compound and exhibits at least one activity of the compound. The compound to which the analogue is compared is known as the "parent" compound. The afore-mentioned activities include, without limitation: binding activity to another compound; inhibitory activity, e.g. enzyme inhibitory activity; toxic effects; activating activity, e.g. enzyme-activating activity. It is not required that the analogue exhibits such an activity to the same extent as the parent compound. A compound is regarded as an analogue within the context of the present application, if it exhibits the relevant activity to a degree of at least 1% (more preferably at least 5%, more preferably at least 10%, more preferably at least 20%, more preferably at least 30%, more preferably at least 40%, and more preferably at least 50%) of the activity of the parent compound. Thus, an "analogue of an amatoxin", as it is used herein, refers to a compound that is structurally related to any one of α-amanitin, β-amanitin, γ-amanitin, ε-amanitin, amanin, amaninamide, amanullin, and amanullinic acid as shown in FIG. 1 and that exhibits at least 1% (more preferably at least 5%, more preferably at least 10%, more preferably at least 20%, more preferably at least 30%, more preferably at least 40%, and more preferably at least 50%) of the inhibitory activity against mammalian RNA polymerase II as compared to at least one of α-amanitin, β-amanitin, γ-amanitin, ε-amanitin, amanin, amaninamide, amanullin, and amanullinic acid. An "analogue of an amatoxin" suitable for use in the present invention may even exhibit a greater inhibitory activity against mammalian RNA polymerase II than any one of α-amanitin, β-amanitin, γ-amanitin, ε-amanitin, amanin, amaninamide, amanullin, or amanullinic acid. The inhibitory activity might be measured by determining the concentration at which 50% inhibition occurs ($IC_{50}$ value). The inhibitory activity against mammalian RNA polymerase II can be determined indirectly by measuring the inhibitory activity on cell proliferation. A suitable assay for measuring inhibition of cell proliferation is described in the examples.

A "semisynthetic analogue" refers to an analogue that has been obtained by chemical synthesis using compounds from natural sources (e.g. plant materials, bacterial cultures, or cell cultures) as starting material. Typically, a "semisynthetic analogue" of the present invention has been synthesized starting from a compound isolated from a mushroom of the Amanita family. In contrast, a "synthetic analogue" refers to an analogue synthesized by so-called total synthesis from small (typically petrochemical) building blocks. Usually, this total synthesis is carried out without the aid of biological processes.

As used herein, an "aptamer conjugate" refers to a target-binding moiety toxin conjugate in which the target-binding moiety is a nucleic acid aptamer according to above alternative (iii).

A "linker" in the context of the present invention refers to a molecule that is connecting two components, each being attached to one end of the linker, and which increases the distance between two components and alleviates steric interference between these components, such as in the present case between the target-binding moiety and the amatoxin. In the absence of a linker, a direct linkage of amatoxin to the target-binding moiety may decrease the ability of the amatoxin to interact with RNA polymerase II. In particular embodiments, a linker has a continuous chains of between 1 and 30 atoms (e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 atoms) in its backbone, i.e. the length of the linker is defined as the shortest connection as measured by the number of atoms or bonds between the amatoxin moiety and the target-binding moiety, wherein one side of the linker backbone has been reacted with the amatoxin and, the other side with a target-binding moiety. In the context of the present invention, a linker preferably is a $C_{1-20}$-alkylene, $C_{1-20}$-heteroalkylene, $C_{2-20}$-alkenylene, $C_{2-20}$-heteroalkenylene, $C_{2-20}$-alkynylene, $C_{2-20}$-heteroalkynylene, cycloalkylene, heterocycloalkylene, arylene, heteroarylene, aralkylene, or a heteroaralkylene group, optionally substituted. The linker may contain one or more structural elements such as carboxamide, ester, ether, thioether, disulfide, urea, thiourea, hydrocarbon moieties and the like. The linker may also contain combinations of two or more of these structural elements. Each one of these structural elements may be present in the linker more than once, e.g. twice, three times, four times, five times, or six times. In some embodiments the linker may comprise a disulfide bond. It is understood that the linker has to be attached either in a single step or in two or more subsequent steps to the amatoxin and the target-binding moiety. To that end the linker to be will carry two groups, preferably at a proximal and distal end, which can (i) form a covalent bond to a group present in one of the components to be linked, preferably an activated group on an amatoxin or the target binding-peptide or (ii) which is or can be activated to form a covalent bond with a group on an amatoxin. Accordingly, it is preferred that chemical groups are at the distal and proximal end of the linker, which are the result of such a coupling reaction, e.g. an ester, an ether, a urethane, a peptide bond etc.

In the context of the present invention, the term "amatoxin" includes all cyclic peptides composed of 8 amino acids as isolated from the genus *Amanita* and described in Wieland, T. and Faulstich H. (Wieland T, Faulstich H., CRC Crit. Rev Biochem. 1978 December; 5(3):185-260), and furthermore includes all chemical derivatives thereof; further all semisynthetic analogues thereof; further all synthetic analogues thereof built from building blocks according to the master structure of the natural compounds (cyclic, 8 amino acids), further all synthetic or semisynthetic analogues containing non-hydroxylated amino acids instead of the hydroxylated amino acids, further all synthetic or semisynthetic analogues, in which the thioether sulfoxide moiety is replaced by a sulfide, sulfone, or by atoms different from sulfur, e.g. a carbon atom as in a carba-analogue of amanitin, in each case wherein any such derivative or analogue is functionally active by inhibiting mammalian RNA polymerase II.

Functionally, amatoxins are defined as peptides or depsipeptides that inhibit mammalian RNA polymerase II. Preferred amatoxins are those with a functional group (e.g. a carboxylic group, an amino group, a hydroxy group, a thiol or a thiol-capturing group) that can be reacted with linker molecules or target-binding moieties as defined above. Amatoxins which are particularly suitable for the conjugates of the present invention are α-amanitin, β-amanitin, γ-amanitin, ε-amanitin, amanin, amaninamide, amanullin, and amanullinic acid as shown in FIG. 1 as well as salts, chemical derivatives, semisynthetic analogues, and synthetic analogues thereof. Particularly preferred amatoxins for use in the present invention are α-amanitin, β-amanitin, and amaninamide.

In the context of the present invention the term "connected to the target-binding moiety via a urea moiety" refers to a connection between the linker and the target-binding moiety, where the target-binding moiety is directly attached to the linker via an —NH—C(O)—NH— group.

In particular embodiments of the present invention, the conjugate has a structure selected from one of the following structures:

amatoxin-γC(O)—NH-L-NH—C(O)—NH-target-binding moiety;

amatoxin-δC—O—C(O)-L-NH—C(O)—NH-target-binding moiety;

amatoxin-δC—O-L-NH—C(O)—NH-target-binding moiety;

amatoxin-δC—O—C(O)—NH-L-NH—C(O)—NH-target-binding moiety; and amatoxin-6'C—O-L-NH—C(O)—NH-target-binding moiety.

In particular embodiments of the present invention, the target-binding moiety is connected to the linker L via an amino group present in the target-binding moiety, wherein said amino group forms part of said urea moiety.

In particular embodiments of the present invention, the amatoxin is selected from α-amanitin, β-amanitin, γ-amanitin, ε-amanitin, amanin, amaninamide, amanullin, or amanullinic acid, or from salts or analogues thereof.

In particular embodiments of the present invention, the linker L comprises one or more groups, particularly one, two or three groups, selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted.

The term "alkylene" refers to a bivalent straight chain saturated hydrocarbon groups having from 1 to 20 carbon atoms, including groups having from 1 to 10 carbon atoms. In certain embodiments, alkylene groups may be lower alkylene groups. The term "lower alkylene" refers to alkylene groups having from 1 to 6 carbon atoms, and in certain embodiments from 1 to 5 or 1 to 4 carbon atoms. Examples of alkylene groups include, but are not limited to, methylene (—$CH_2$—), ethylene (—$CH_2$—$CH_2$—), n-propylene, n-butylene, n-pentylene, and n-hexylene.

The term "alkenylene" refers to bivalent straight chain groups having 2 to 20 carbon atoms, wherein at least one of the carbon-carbon bonds is a double bond, while other bonds may be single bonds or further double bonds. The term "alkynylene" herein refers to groups having 2 to 20 carbon atoms, wherein at least one of the carbon-carbon bonds is a triple bond, while other bonds may be single, double or further triple bonds. Examples of alkenylene groups include ethenylene (—CH═CH—), 1-propenylene, 2-propenylene, 1-butenylene, 2-butenylene, 3-butenylene, and the like. Examples of alkynylene groups include ethynylene, 1-propynylene, 2-propynylene, and so forth.

As used herein, "cycloalkylene" is intended to refer to a bivalent ring being part of any stable monocyclic or polycyclic system, where such ring has between 3 and 12 carbon atoms, but no heteroatom, and where such ring is fully saturated, and the term "cycloalkenylene" is intended to refer to a bivalent ring being part of any stable monocyclic or polycyclic system, where such ring has between 3 and 12 carbon atoms, but no heteroatom, and where such ring is at least partially unsaturated (but excluding any arylene ring). Examples of cycloalkylenes include, but are not limited to, cyclopropylene, cyclobutylene, cyclopentylene, cyclohexylene, and cycloheptylene. Examples of cycloalkenylenes include, but are not limited to, cyclopentenylene and cyclohexenylene.

As used herein, the terms "heterocycloalkylene" and "heterocycloalkenylene" are intended to refer to a bivalent ring being part of any stable monocyclic or polycyclic ring system, where such ring has between 3 and about 12 atoms, and where such ring consists of carbon atoms and at least one heteroatom, particularly at least one heteroatom independently selected from the group consisting of N, O and S, with heterocycloalkylene referring to such a ring that is fully saturated, and heterocycloalkenylene referring to a ring that is at least partially unsaturated (but excluding any arylene or heteroarylene ring).

The term "arylene" is intended to mean a bivalent ring or ring system being part of any stable monocyclic or polycyclic system, where such ring or ring system has between 3 and 20 carbon atoms, but has no heteroatom, which ring or ring system consists of an aromatic moiety as defined by the "4n+2" π electron rule, including phenylene.

As used herein, the term "heteroarylene" refers to a bivalent ring or ring system being part of any stable mono- or polycyclic system, where such ring or ring system has between 3 and 20 atoms, which ring or ring system consists of an aromatic moiety as defined by the "4n+2" π electron rule and contains carbon atoms and one or more nitrogen, sulfur, and/or oxygen heteroatoms.

In the context of the present invention, the term "substituted" is intended to indicate that one or more hydrogens present in the backbone of a linker is replaced with a selection from the indicated group(s), provided that the indicated atom's normal valency, or that of the appropriate atom of the group that is substituted, is not exceeded, and that the substitution results in a stable compound. The term "optionally substituted" is intended to mean that the linker is either unsubstituted or substituted, as defined herein, with one or more substituents, as defined herein. When a substituent is a keto (or oxo, i.e. =O) group, a thio or imino group or the like, then two hydrogens on the linker backbone atom are replaced. Exemplary substituents include, for example, alkyl, alkenyl, alkynyl, cycloalkyl, heterocycloalkyl, aryl, heteroaryl, aralkyl, heteroaralkyl, acyl, aroyl, heteroaroyl, carboxyl, alkoxy, aryloxy, acyloxy, aroyloxy, heteroaroyloxy, alkoxycarbonyl, halogen, (thio)ester, cyano, phosphoryl, amino, imino, (thio)amido, sulfhydryl, alkylthio, acylthio, sulfonyl, a sulfate, a sulfonate, a sulfamoyl, a sulfonamido, nitro, azido, haloalkyl, including perfluoroalkyl (such as trifluoromethyl), haloalkoxy, alkylsulfanyl, alkylsulfinyl, alkylsulfonyl, alkylsulfonylamino, arylsulfonoamino, phosphoryl, phosphate, phosphonate, phosphinate, alkylcarboxy, alkylcarboxyamide, oxo, hydroxy, mercapto, amino (optionally mono- or di-substituted, e.g. by alkyl, aryl, or heteroaryl), imino, carboxamide, carbamoyl (optionally mono- or di-substituted, e.g. by alkyl, aryl, or heteroaryl), amidino, aminosulfonyl, acylamino, aroylamino, (thio)ureido, arylthio)ureido, alkyl (thio)ureido, cycloalkyl(thio)ureido, aryloxy, aralkoxy, or $—O(CH_2)_n—OH$, $—O(CH_2)_n—NH_2$, $—O(CH_2)_nCOOH$, $—(CH_2)_nCOOH$, $—C(O)O(CH_2)_nR$, $—(CH_2)_nN(H)C(O)OR$, or $—N(R)S(O)_2R$ wherein n is 1-4 and R is independently selected from hydrogen, -alkyl, -alkenyl, -alkynyl, -cycloalkyl, -cycloalkenyl, —(C-linked-heterocycloalkyl), —(C-linked-heterocycloalkenyl), -aryl, and -heteroaryl, with multiple degrees of substitution being allowed. It will be understood by those skilled in the art that substituents, such as heterocycloalkyl, aryl, heteroaryl, alkyl, etc., or functional groups such as —OH, —NHR etc., can themselves be substituted, if appropriate. It will also be understood by those skilled in the art that the substituted moieties themselves can be substituted as well when appropriate.

In particular embodiments of the present invention, the linker L, particularly the linker L as shown in section [0042] or section [0081], comprises m groups selected from the list of: alkylene, alkenylene, alkynylene, cycloalkylene, heteroalkylene, heteroalkenylene, heteroalkynylene, heterocycloalkylene, arylene, heteroarylene, aralkylene, and a heteroaralkylene group, wherein each group may optionally be independently substituted, the linker further comprises n moiety independently selected from one of the following moieties: a disulfide (—S—S—), an ether (—O—), a thioether (—S—), an amine (—NH—), an ester (—O—C(=O)— or —C(=O)—O—), a carboxamide (—NH—C(=O)— or —C(=O)—NH—), a urethane (—NH—C(=O)—O— or —O—C(=O)—NH—), and a urea moiety (—NH—C(=O)—NH—), wherein m=n+1. In particular embodiments, m is 2 and n is 1, or m is 3 and n is 2. In particular embodiments, the linker comprises 2 or 3 unsubstituted alkylene groups, and 1 or 2, respectively, disulfide, ether, thioether, amine, ester, carboxamide, urethane or urea moieties linking the unsubstituted alkylene groups.

In particular embodiments, the linker L, particularly the linker L as shown in section [0042], is a linear chain of between 2 and 20 atoms independently selected from C, O, N and S, particularly between 2 and 16 atoms, more particularly between 5 and 14 atoms, and even more particularly between 6 and 12 atoms. In particular embodiments, at least 60% of the atoms in the linear chain are C atoms. In particular embodiments, the atoms in the linear chain are linked by single bonds.

In particular embodiments, the C atoms in the linear chain are independently part of optionally substituted methylene groups ($—CH_2—$). In particular such embodiments, the optional substituents are independently selected from halogen and $C_{1-6}$-alkyl. particularly methyl.

In particular embodiments, the linker L, particularly the linker L as shown in section [0042] or section [0081], is selected from the following group of linkers:

amatoxin side: $—(CH_2)_2—$ target-binding moiety side
amatoxin side: $—(CH_2)_3—$ target-binding moiety side
amatoxin side: $—(CH_2)_4—$ target-binding moiety side
amatoxin side: $—(CH_2)_5—$ target-binding moiety side
amatoxin side: $—(CH_2)_6—$ target-binding moiety side
amatoxin side: $—(CH_2)_7—$ target-binding moiety side
amatoxin side: $—(CH_2)_8—$ target-binding moiety side
amatoxin side: $—(CH_2)_9—$ target-binding moiety side
amatoxin side: $—(CH_2)_{10}—$ target-binding moiety side
amatoxin side: $—(CH_2)_{11}—$ target-binding moiety side
amatoxin side: $—(CH_2)_{12}—$ target-binding moiety side
amatoxin side: $—(CH_2)_{16}—$ target-binding moiety side
amatoxin side: $—(CH_2)_2—S—S—(CH_2)_2—$ target-binding moiety side
amatoxin side: $—(CH_2)_3—S—S—(CH_2)_2—$ target-binding moiety side
amatoxin side: $—(CH_2)_2—S—S—(CH_2)_3—$ target-binding moiety side
amatoxin side: $—(CH_2)_3—S—S—(CH_2)_3—$ target-binding moiety side
amatoxin side: $—(CH_2)_4—S—S—(CH_2)_4—$ target-binding moiety side
amatoxin side: $—(CH_2)_2—CMe_2\text{-}S—S—(CH_2)_2—$ target-binding moiety side
amatoxin side: $—(CH_2)_2—S—S\text{-}CMe_2\text{-}(CH_2)_2—$ target-binding moiety side
amatoxin side: $—(CH_2)_2—O—(CH_2)_2—$ target-binding moiety side
amatoxin side: $—(CH_2)_2—O—(CH_2)_2—O—(CH_2)_2—$ target-binding moiety side
amatoxin side: $—(CH_2)_2—O—(CH_2)_2—O—(CH_2)_2—O—(CH_2)_2—$ target-binding moiety side
amatoxin side: $—(CH_2)_2—O—(CH_2)_2—O—(CH_2)_2—O—(CH_2)_2—O—(CH_2)_2—$ target-binding moiety side In particular embodiments of the present invention the target-binding moiety specifically binds to an epitope that is present on a tumour cell.

In particular embodiments of the present invention the target-binding moiety specifically binds to an epitope of Her-2/neu or epithelial cell adhesion molecule (EpCAM).

In particular embodiments of the present invention the target-binding moiety is selected from the group consisting of: antibody or antigen-binding fragment thereof, antibody-like protein, and nucleic acid aptamer.

In particular embodiments of the present invention the antibody or the antigen-binding fragment thereof is selected from a diabody, a tetrabody, a nanobody, a chimeric antibody, a deimmunized antibody, a humanized antibody or a human antibody.

In particular embodiments of the present invention the antigen binding fragment is selected from the group consisting of Fab, $F(ab')_2$, Fd, Fv, single-chain Fv, and disulfide-linked Fvs (dsFv).

In particular embodiments, the antibody is herceptin or HEA125, or an antibody fragment comprising the antigen binding fragment of herceptin or HEA125.

In particular embodiments, more than one amatoxin molecule is coupled to one target-binding moiety. An increase of the number of amatoxins per conjugate will also increase the toxicity. Accordingly, in a particular embodiment the ratio of target-binding moiety to amatoxin is between 1 target-binding moiety to between 2 and 15 amatoxin molecules, particularly 2, 3, 4, 5, 6, 7, 8, 9, 10, 11, 12, 13, 14, or 15. For the purpose of the calculation of the ratio in case of antibody dimers such as IgGs, the dimer is considered as one target-binding moiety.

In particular embodiments of the present invention, the conjugate is for use as a medicament.

In particular embodiments of the present invention, the conjugate is for the treatment of cancer in a patient, wherein the cancer is selected from the group consisting of pancreatic cancer, cholangiocarcinoma, breast cancer, colorectal cancer, lung cancer, prostate cancer, ovarian cancer, stomach cancer, kidney cancer, malignant melanoma, leukemia, and malignant lymphoma.

As used herein, a "patient" means any mammal or bird who may benefit from a treatment with the target-binding moiety toxin conjugates described herein. Preferably, a "patient" is selected from the group consisting of laboratory animals (e.g. mouse or rat), domestic animals (including e.g. guinea pig, rabbit, chicken, pig, sheep, goat, camel, cow, horse, donkey, cat, or dog), or primates including human beings. It is particularly preferred that the "patient" is a human being.

As used herein, "treat", "treating" or "treatment" of a disease or disorder means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the treatment may comprise administering a conjugate or a pharmaceutical composition according to the present invention to a patient, wherein "administering" includes in vivo administration, as well as administration directly to tissue ex vivo, such as vein grafts.

In particular embodiments, a therapeutically effective amount of the conjugate of the present invention is used.

A "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

In a second aspect the present invention relates to a pharmaceutical composition comprising the conjugate according to the present invention, further comprising one or more pharmaceutically acceptable diluents, carriers, excipients, fillers, binders, lubricants, glidants, disintegrants, adsorbents; and/or preservatives.

"Pharmaceutically acceptable" means approved by a regulatory agency of the Federal or a state government or listed in the U.S. Pharmacopeia or other generally recognized pharmacopeia for use in animals, and more particularly in humans.

In particular embodiments, the pharmaceutical composition is used in the form of a systemically administered medicament. This includes parenterals, which comprise among others injectables and infusions. Injectables are formulated either in the form of ampoules or as so called ready-for-use injectables, e.g. ready-to-use syringes or single-use syringes and aside from this in puncturable flasks for multiple withdrawal. The administration of injectables can be in the form of subcutaneous (s.c.), intramuscular (i.m.), intravenous (i.v.) or intracutaneous (i.c.) application. In particular, it is possible to produce the respectively suitable injection formulations as a suspension of crystals, solutions, nanoparticular or a colloid dispersed systems like, e.g. hydrosols.

Injectable formulations can further be produced as concentrates, which can be dissolved or dispersed with aqueous isotonic diluents. The infusion can also be prepared in form of isotonic solutions, fatty emulsions, liposomal formulations and micro-emulsions. Similar to injectables, infusion formulations can also be prepared in the form of concentrates for dilution. Injectable formulations can also be applied in the form of permanent infusions both in in-patient and ambulant therapy, e.g. by way of mini-pumps.

It is possible to add to parenteral drug formulations, for example, albumin, plasma, expander, surface-active substances, organic diluents, pH-influencing substances, complexing substances or polymeric substances, in particular as substances to influence the adsorption of the target-binding moiety toxin conjugates of the invention to proteins or polymers or they can also be added with the aim to reduce the adsorption of the target-binding moiety toxin conjugates of the invention to materials like injection instruments or packaging-materials, for example, plastic or glass.

The target-binding moiety toxin conjugates of the invention can be bound to microcarriers or nanoparticles in parenterals like, for example, to finely dispersed particles based on poly(meth)acrylates, polylactates, polyglycolates, polyamino acids or polyether urethanes. Parenteral formulations can also be modified as depot preparations, e.g. based on the "multiple unit principle", if the target-binding moiety toxin conjugates of the invention are introduced in finely dispersed, dispersed and suspended form, respectively, or as a suspension of crystals in the medicament or based on the "single unit principle" if the target-binding moiety toxin conjugate of the invention is enclosed in a formulation, e.g. in a tablet or a rod which is subsequently implanted. These implants or depot medicaments in single unit and multiple unit formulations often consist of so called biodegradable polymers like e.g. polyesters of lactic acid and glycolic acid, polyether urethanes, polyamino acids, poly(meth)acrylates or polysaccharides.

Adjuvants and carriers added during the production of the pharmaceutical compositions of the present invention formulated as parenterals are preferably aqua sterilisata (sterilized water), pH value influencing substances like, e.g. organic or inorganic acids or bases as well as salts thereof, buffering substances for adjusting pH values, substances for isotonization like e.g. sodium chloride, sodium hydrogen carbonate, glucose and fructose, tensides and surfactants, respectively, and emulsifiers like, e.g. partial esters of fatty acids of polyoxyethylene sorbitans (for example, Tween®) or, e.g. fatty acid esters of polyoxyethylenes (for example, Cremophor®), fatty oils like, e.g. peanut oil, soybean oil or castor oil, synthetic esters of fatty acids like, e.g. ethyl oleate, isopropyl myristate and neutral oil (for example, Miglyol®) as well as polymeric adjuvants like, e.g. gelatine, dextran, polyvinylpyrrolidone, additives which increase the solubility of organic solvents like, e.g. propylene glycol, ethanol, N,N-dimethylacetamide, propylene glycol or complex forming substances like, e.g. citrate and urea, preservatives like, e.g. benzoic acid hydroxypropyl ester and methyl ester, benzyl alcohol, antioxidants like e.g. sodium sulfite and stabilizers like e.g. EDTA.

When formulating the pharmaceutical compositions of the present invention as suspensions in a preferred embodiment thickening agents to prevent the setting of the target-binding moiety toxin conjugates of the invention or, tensides and polyelectrolytes to assure the resuspendability of sediments and/or complex forming agents like, for example, EDTA are added. It is also possible to achieve complexes of the active ingredient with various polymers. Examples of such polymers are polyethylene glycol, polystyrene, carboxymethyl cellulose, Pluronics® or polyethylene glycol sorbit fatty acid ester. The target-binding moiety toxin conjugates of the invention can also be incorporated in liquid formulations in the form of inclusion compounds e.g. with cyclodextrins. In particular embodiments dispersing agents can be added as further adjuvants. For the production of lyophilisates scaffolding agents like mannite, dextran, saccharose, human albumin, lactose, PVP or varieties of gelatine can be used.

In a further aspect the present invention is directed to a method of treating pancreatic cancer, cholangiocarcinoma, breast cancer, colorectal cancer, lung cancer, prostate cancer, ovarian cancer, stomach cancer, kidney cancer, malignant melanoma, leukemia, or malignant lymphoma in a patient in need thereof, comprising administering to the patient an effective amount of a conjugate or pharmaceutical composition of the present invention.

In another aspect, the present invention relates to an amatoxin-conjugation molecule as an intermediate for the synthesis of the conjugates of the present invention, wherein the amatoxin-conjugation molecule comprises a linker L connected to an amatoxin via (i) the γ C-atom of amatoxin amino acid 1, particularly via an amide linkage;

(ii) an oxygen atom bound to the δ C-atom of amatoxin amino acid 3, particularly via an ester linkage, an ether linkage or a urethane linkage; or (iii) the 6' C-atom of amatoxin amino acid 4, particularly via an oxygen atom bound to the 6' C-atom of amatoxin amino acid 4;

in each case wherein the linker L comprises a carbamic acid derivative —NH—C(O)—X, wherein X is a leaving group that can be replaced by a primary amine of a target-binding moiety.

In one embodiment, the amatoxin-conjugation molecule has a structure selected from one of the following structures:

(i) amatoxin-γC(O)—NH-L-NH—C(O)—X;

(ii) amatoxin-δC—O—C(O)-L-NH—C(O)—X;

(iii) amatoxin-δC—O-L-NH—C(O)—X;

(iv) amatoxin-δC—O—C(O)—NH-L-NH—C(O)—X; and (v) amatoxin-δ'C—O-L-NH—C(O)—X.

In certain embodiments, the amatoxin is selected from α-amanitin, β-amanitin, γ-amanitin, ϵ-amanitin, amanin, amaninamide, amanullin, or amanullinic acid, or from salts or analogues thereof.

In certain embodiments, the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, optionally substituted.

In certain embodiments, the linker L comprises a moiety selected from one of the following moieties: a disulfide, an ether, an amine, an ester, a carboxamide, a urethane, and a urea moiety.

In certain embodiments, the functional group X is selected from: -$^{t}$butyloxy, -succinimidyloxy, -1-O-succinimidyloxy-3-sulfonate (-Sulfo-NHS), —O-(4-nitrophenyloxy), —O-(3-nitrophenyloxy), —O-(2,4-dinitrophenyloxy), —O-(2,4-dichloro-6-nitrophenyloxy), -pentafluorophenyloxy, -pentachlorophenyloxy, —O-(2,4,5-trichlorophenyloxy), —O-(3,4-dihydro-3-hydroxy-4-oxo-1,2,3-benzotriazine-3-yl), —O-(endo-1-hydroxy-5-norbornene-2,3-dicarboximide-1-yl), -1-phthalimidoyloxy, -1-benzotriazolyloxy, -1-(7-aza-benzotriazolyl)oxy), and —N-imidazolyl.

In yet another aspect, the present invention relates to a method for synthesizing an amatoxin conjugate of the present invention, comprising the step of reacting an amatoxin-conjugation molecule of the present invention with a target-binding moiety comprising a primary amino group.

EXAMPLES

In the following, the invention is explained in more detail by non-limiting examples:

Example 1

Synthesis of α-Amanitin Herceptin Antibody Conjugate Her-DSC-30.0134

1.1 Synthesis of 6'-NH-boc-(6-aminohexyl)-α-amanitin HDP 30.0132

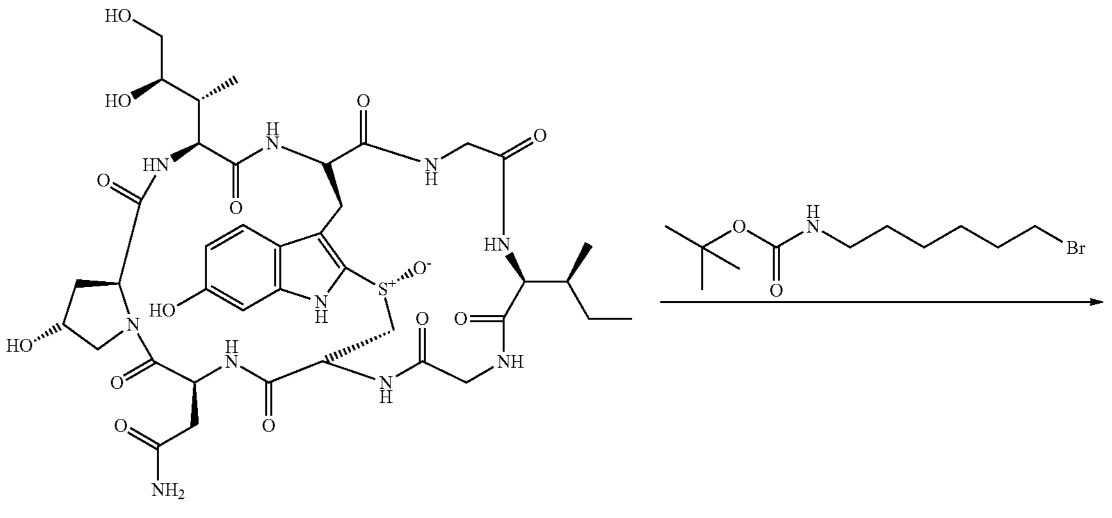

α-amanitin

-continued

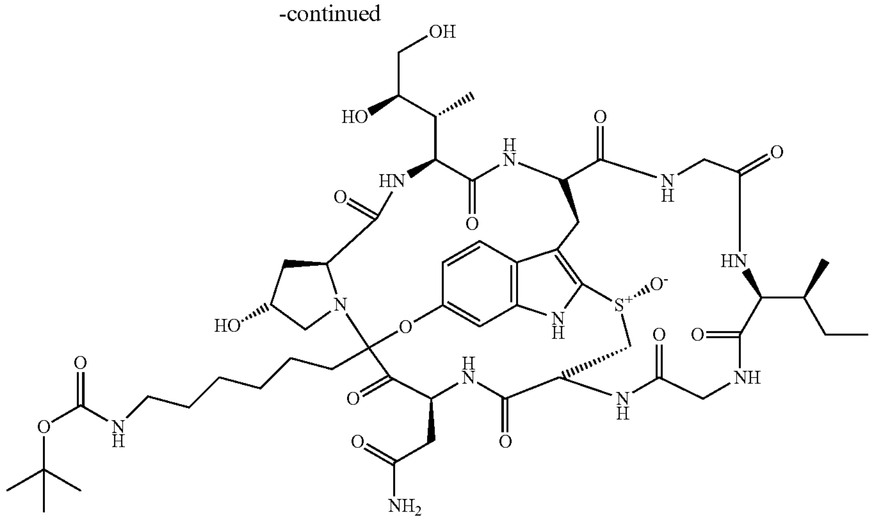

HDP 30.0132

Under argon and at room temperature 30.00 mg (32.6 μmol) of vacuum dried α-amanitin were dissolved in 900 μl dry dimethyl sulfoxide (DMSO). Potassium tert.-butylate 3.66 mg (32.6 μmol) and 73.18 mg (261.2 μmol, 8 eq.) NH-Boc-aminohexylbromide (Fluka 89171) were added. After 6 h at room temperature the reaction mixture was acidified to pH=5 with 50 μl of a 0.33 M acetic acid solution in DMSO. Volatiles were evaporated in vacuum and the residue was dissolved in 1000 μl methanol and diluted with 20 ml diethyl ether. The precipitate was collected and taken up in 1000 μl methanol. This solution was diluted with 1000 μl water and used for the purification on a LaPrep-HPLC:

(column: Kromasil 100-C18, 250 mm×20 mm, 10 μm, with methanol/water (0.05% TFA), flow: 26 ml/min, detection at λ=295 nm).

Solvent A: 95% water:5% methanol:0.05% trifluoroacetic acid

Solvent B: 10% water:90% methanol:0.05% trifluoroacetic acid gradient: 0-5 min 100% A; 5-20 min 0% A; 20-40 min 0% A The fraction with the retention time of 19.8 min was collected and the solvents were evaporated.

15.9 mg (43% yield) of a powder. MS: 1119 ($M+H^+$); 1141 ($M+Na^+$)

1.2 Synthesis of 6'-(-6-aminohexyl)-α-amanitin HDP 30.0134

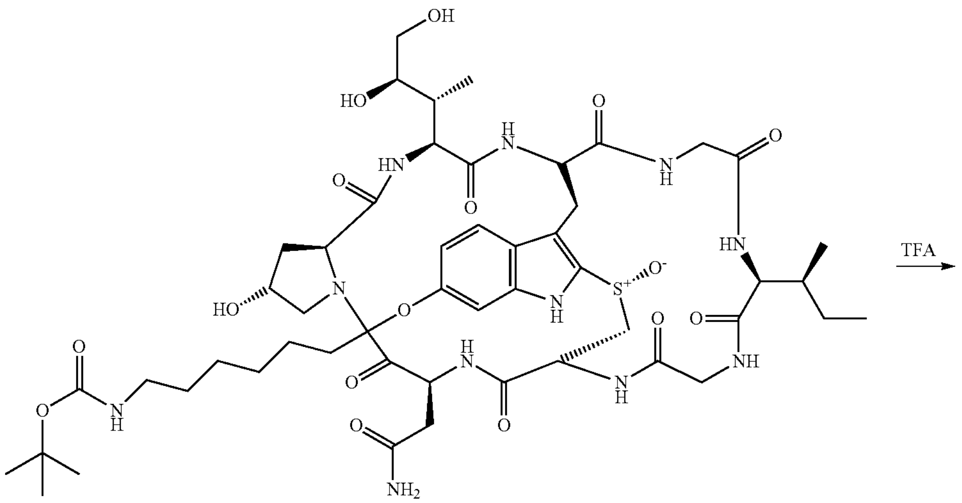

HDP 30.0132

-continued

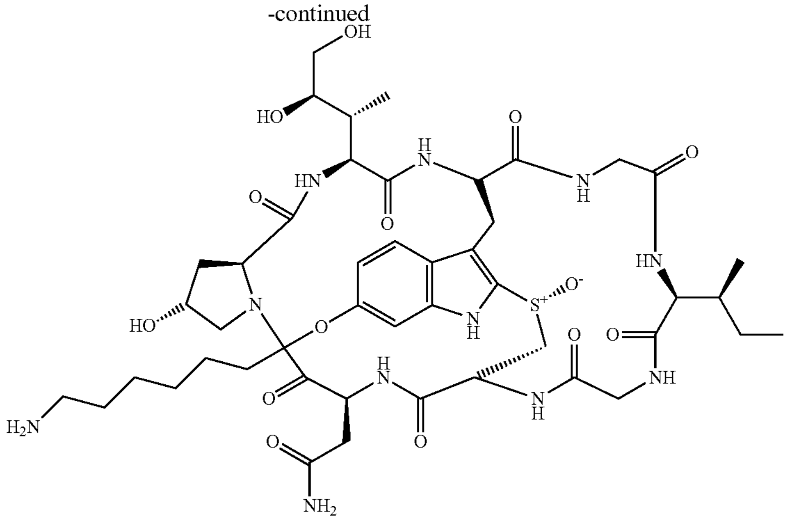

HDP 30.0134

9.90 mg (8.85 μmol) 6'-NH-boc-6-aminohexyl-α-amanitin HDP 30.0132 were dissolved in 250 μl trifluoroacetic acid. The reaction mixture was stirred under argon at ambient temperature. After 2 min the acid was removed in vacuum at 20° C. and the residue dried. The crude amanitin ether was purified on a LaPrep-HPLC:

(column: Kromasil 100-C18, d=10 mm, 10 μm, with methanol/water (0.05% TFA), flow: 6 ml/min, detection at λ=295 nm).

Solvent A: 95% water:5% methanol:0.05% trifluoroacetic acid

Solvent B: 10% water:90% methanol:0.05% trifluoroacetic acid

Gradient: 0-5 min 100% A; 5-25 min 50% A; 25-30 min 0% A; 30-35 min 0% A; 35-40 min 100% A, 40-45 min 100% A The fractions with the same retention time (14.5 min) were collected and the solvents evaporated.

9.10 mg (99% yield) of a white powder. MS: 1019 (M+H$^+$); 1041 (M+Na$^+$)

1.3 Synthesis of the HDP 30.0134 Antibody Derivative Her-DSC-30.0134

Scheme 1

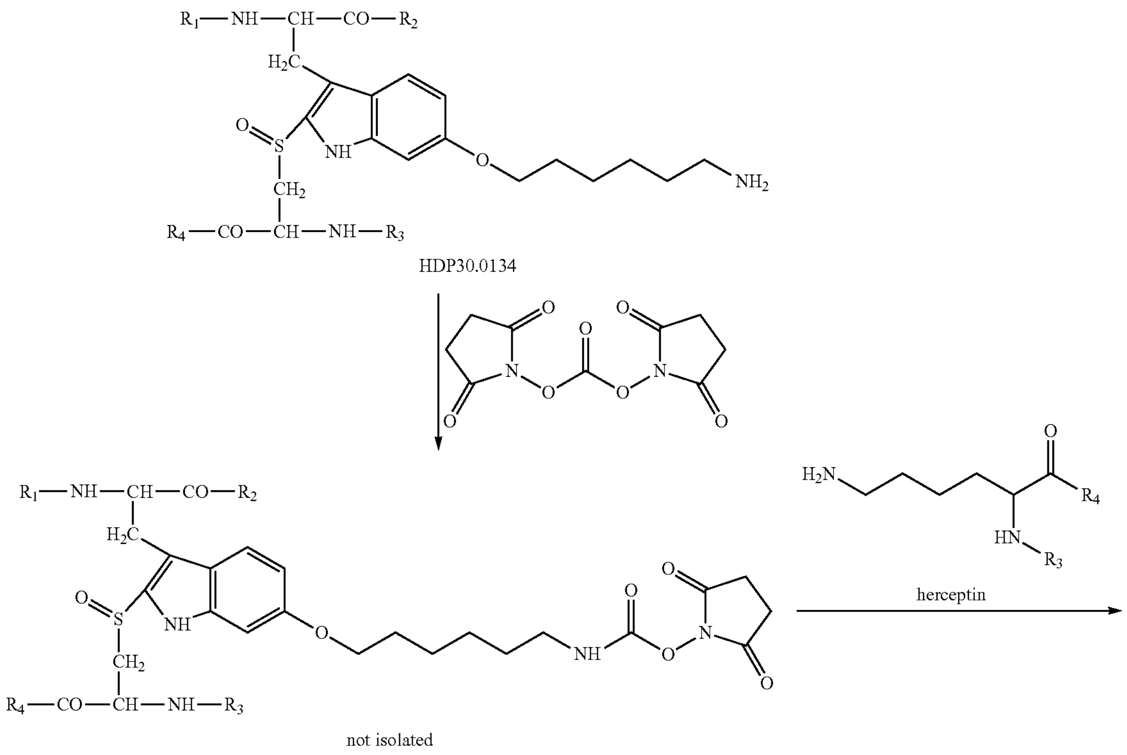

-continued

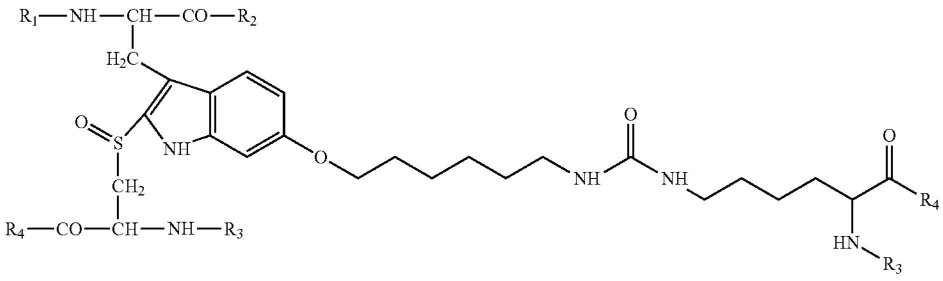

Her-DSC-30.0134

In Scheme 1 (and other schemes shown in the examples), herceptin is represented by a schematic formula showing one lysine side chain with R3 and R4 representing the remaining part of the herceptin antibody protein.

1.3.1 Synthesis of 6"-(–6-aminohexyl-6-hydroxysuccinimidyl)-α-amanitin-Herceptin Conjugate Her-DSC-30.0134 with Different Toxin Payloads (Table 2)

5.00 mg 6"-(–6-aminohexyl)-α-amanitin HDP 30.0134 were dissolved in 538 μl dry dimethylformamide (DMF). Under argon and stirring at room temperature 18.6 μl of a solution of dihydroxysuccinimido carbonate (DSC) in DMF (2.56 mg in 100 μl DMF) and 10.0 μl triethylamine were added at once. The reaction mixture was stirred at room temperature. After 12 h, 60 ml cold diethyl ether were added. The precipitate of α-amanitin-6'-(–6-aminohexyl-6-hydroxysuccinimidyl carbonate) was collected and washed several times with diethyl ether and dried in vacuum. The remaining solid was taken up in 750 μl DMF=solution A.

114.0 mg Herceptin were dissolved in 19.0 ml phosphate buffered saline (PBS, pH=7.4)=solution B.

TABLE 2

3 samples of the Herceptin solution are treated with different amounts of the α-amanitin-6'-(-6-aminohexyl-6-hydroxysuccinimidyl carbonate) solutions:

| Solution A | Solution B | Herceptin:amanitin-linker payload | Sample name |
|---|---|---|---|
| 152 μl | 11.0 ml | 1:1.3 | Her-DSC-30.0134 [1.3] |
| 242 μl | 5.0 ml | 1:4.3 | Her-DSC-30.0134 [4.3] |
| 290 μl | 3.0 ml | 1:7.5 | Her-DSC-30.0134 [7.5] |

The three Herceptin amanitin-linker solutions were shaken at 4° C. for 14 h and separated each by Sephadex G-25 gel filtration chromatography (XK-16 column; 2 ml/min). The G-25 column was prewashed with 500 ml PBS solutions, pH=7.4. The Her-DSC-30.0134 conjugate fraction was detected by UV absorption. Protein concentration was determined by RotiQuant-Assay (Carl Roth; Germany). Amanitin payload of Herceptin was determined by determination of UV absorption at A=280 nm and A=310 nm.

Example 2

Synthesis of α-Amanitin Herceptin Antibody Conjugate Her-DSC-30.0256

2.1 Preparation of 1-Isocyanato-6-BocNH-aminohexane HDP 30.0247

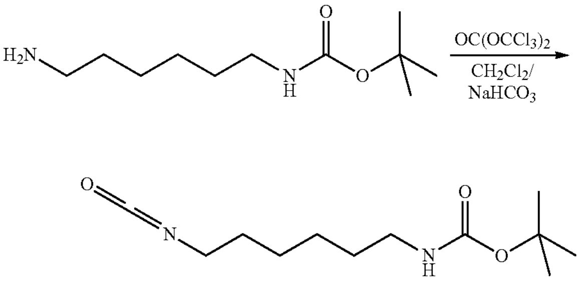

HDP 30.0247

2.50 g (11.56 mmol) NH-Boc-1,6-hexamethylenediamine (Aldrich 79229) were dissolved in 35 ml dichloromethane. 35 ml of a saturated NaHCO3 solution in water were added. After addition of 1.143 g (3.85 mmol) bis-(trichloromethyl carbonate (triphosgene) the reaction mixture was vigorously stirred at 0° C. for 30 min. The organic layer was separated and the aqueous phase extracted three times with 15 ml dichloromethane. The combined organic phases were dried over MgSO4 and evaporated. The oily residue was fractionated at 150° C. and 0.59 mbar in a Kugelrohr oven. 2.23 g (80%) of a clear oil MS: 242 (M+)

2.2 Synthesis of δ-O—(NH-boc-6-aminohexylcarbamoyl)-α-amanitin HDP 30.0253

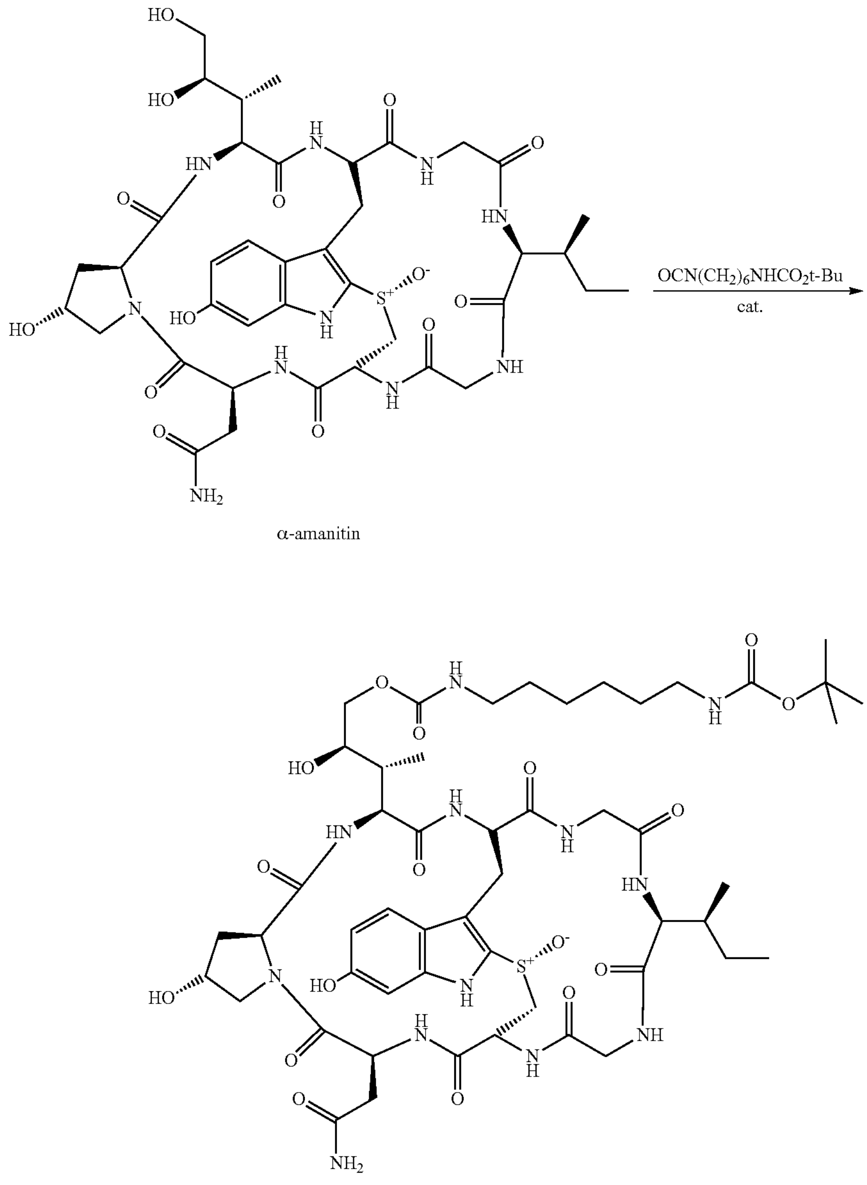

α-amanitin

HDP 30.0253 cat.: dibutyl dilaurylstannate n-$Bu_2Sn[OCO(CH_2)_{10}CH_3]_2$

Under an atmosphere of argon 13.43 mg (14.6 μmol) vacuum dried α-amanitin were dissolved in 1000 μl dry dimethyl formamide (DMF). 7.08 mg (29.2 μmol) NH-Boc-6-isocyanato aminohexane and 18.46 mg (29.2 μmol) di-butyl dilaurylstannate were added and the reaction mixture stirred at ambient temperature. After 23 h additional 13.43 mg (14.6 μmol) NH-Boc-6-isocyanato aminohexane were added. After 52 h the reaction mixture was hydrolyzed with 200 μl methanol and evaporated to dryness. The residue was dissolved in 1200 μl DMSO and purified on a LaPrep-HPLC column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water: 95% methanol. Gradient: 0-5 min 100% A; 5-20 min 0% A; 20-25 min 0% A; 25-27 min 100% A; 27-35 min 100% A. The fractions with the same retention time were collected and the solvents evaporated.

9.06 mg (53% yield) of a white solid. MS: 1161 ($M+H^+$); 1183 ($M+Na^+$)

2.3 Synthesis of δ-O-6-aminohexylcarbamoyl)-α-amanitin HDP 30.0256

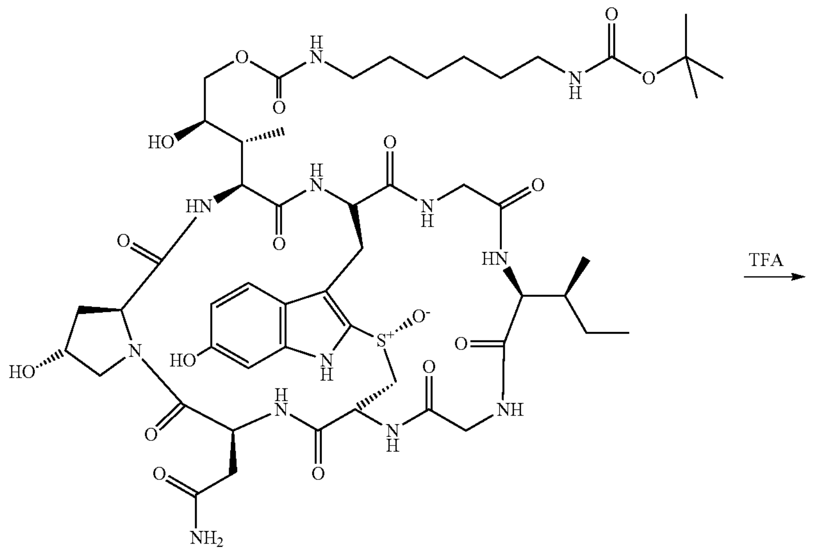

HDP 30.0253

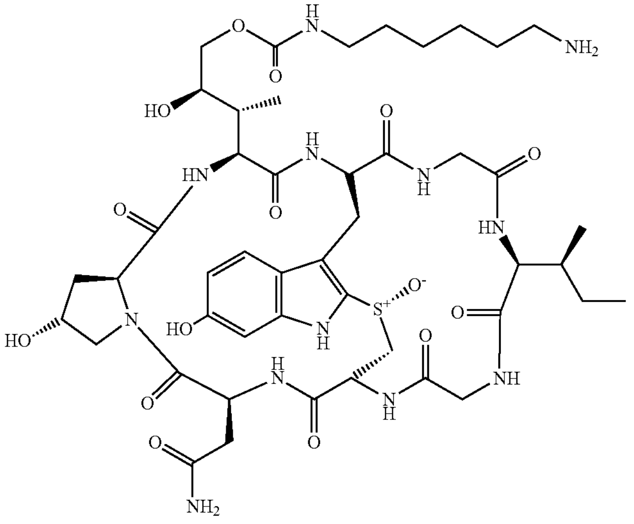

HDP 30.0256

9.06 mg (7.8 μmol) HDP 30.0253 were dissolved in 250 μl trifluoroacetic acid and stirred for 2 min at ambient temperature. The reaction mixture was evaporated to dryness and the residue co-evaporated 2 times with 1.5 ml acetonitrile. The solid was purified on a LaPrep-HPLC:

column: Kromasil 100-C18, 10 μm, 250 mm×20 mm, with acetonitrile/water, flow: 26 ml/min, detection at λ=295 nm. Solvent A: 95% water: 5% acetonitrile. Solvent B: 5% water: 95% acetonitrile. Gradient: 0-5 min 100% A; 5-20 min 0% A; 20-25 min 0% A; 25-27 min 100% A; 27-35 min 100% A.

The fractions with the retention time between 12-17 min were collected and evaporated to a white solid.

8.75 mg (95% yield). MS: (1061 $M+H^+$); 1083 ($M+Na^+$)

2.4 Synthesis of the HDP 30.0256 Antibody Derivative Her-DSC-30.0256
Scheme 2
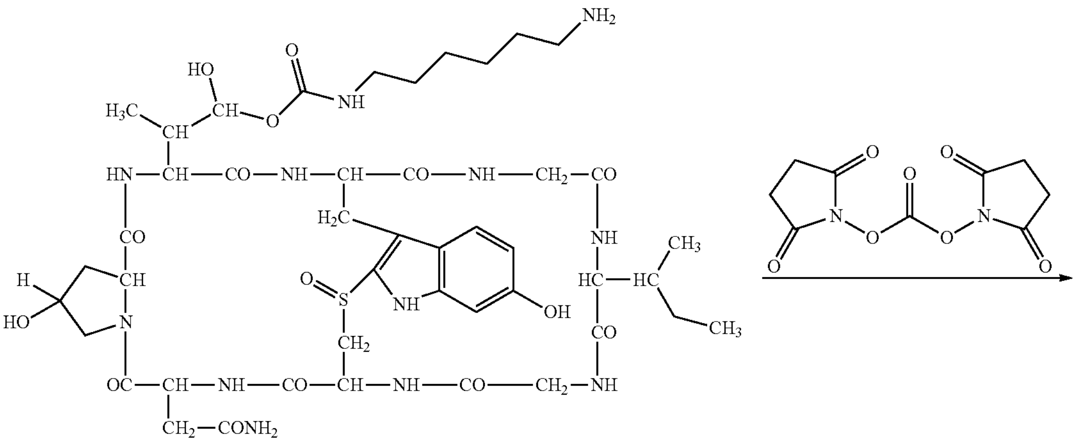
HDP 30.0256
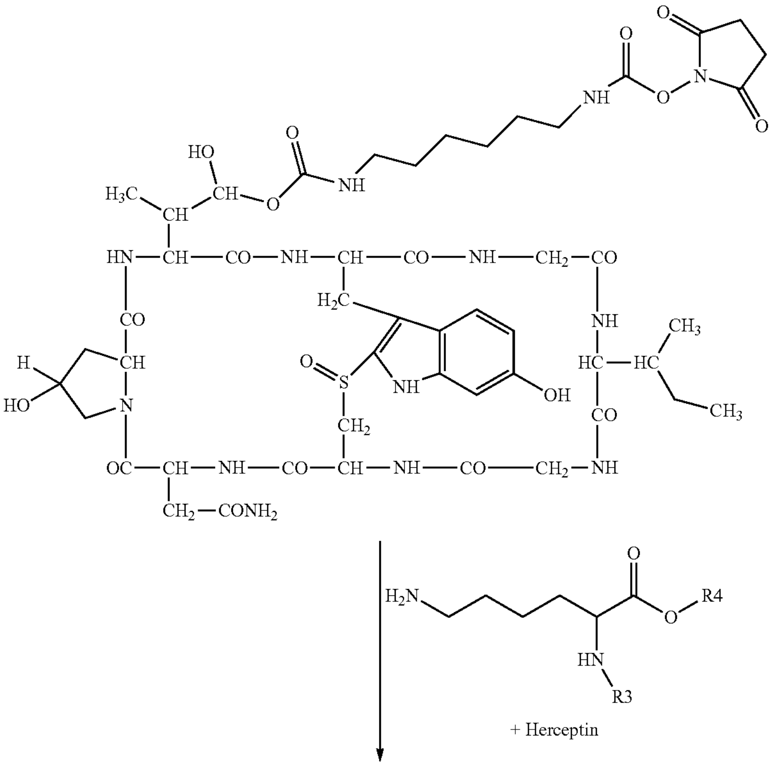

-continued

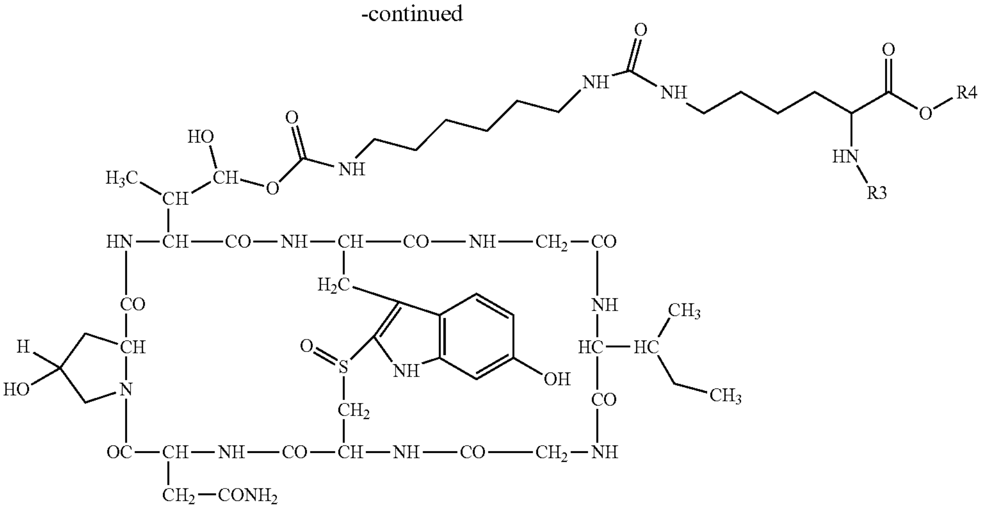

Her-DSC-30.0256

2.4.1 Synthesis of HDP-30.0256 Herceptin Conjugate Her-DSC-30.0256 [3.3]

1.00 mg HDP 30.0256 was dissolved in 108 μl dry dimethylformamide (DMF). Under argon and stirring at room temperature 10.0 μl of a solution of dihydroxysuccinimido carbonate (DSC) in DMF (2.56 mg in 100 μl DMF) and 2.0 μl triethylamine were added at once. The reaction mixture was stirred at room temperature. After over night incubation, 30 ml cold diethyl ether were added. The precipitate was collected and washed several times with diethyl ether and dried in vacuum. The remaining solid was taken up in 143 μl DMF=solution A. 12.0 mg Herceptin were dissolved in 6.0 ml phosphate buffered saline (PBS, pH=7.4)=solution B. Solution A and solution B were combined. The Herceptin amanitin-linker solution was shaken at 4° C. for 14 h and separated by Sephadex G-25 gel filtration chromatography (XK-16 column; 2 ml/min). The G-25 column was prewashed with 500 ml PBS solution, pH=7.4. The Her-DSC-30.0256 conjugate fraction was detected by UV absorption. Protein concentration was determined by RotiQuant-Assay (Carl Roth; Germany). Amanitin payload of Herceptin was determined by determination of UV absorption at A=280 nm and A=310 nm. A toxin payload of 3.3 amanitin molecules for each Herceptin molecule was calculated.

Example 3

Synthesis of □-Amanitin Herceptin Antibody Conjugate Her-DSC-30.0304

3.1 BocNH-hexamethylenediamino-β-amanitin amide HDP 30.0299

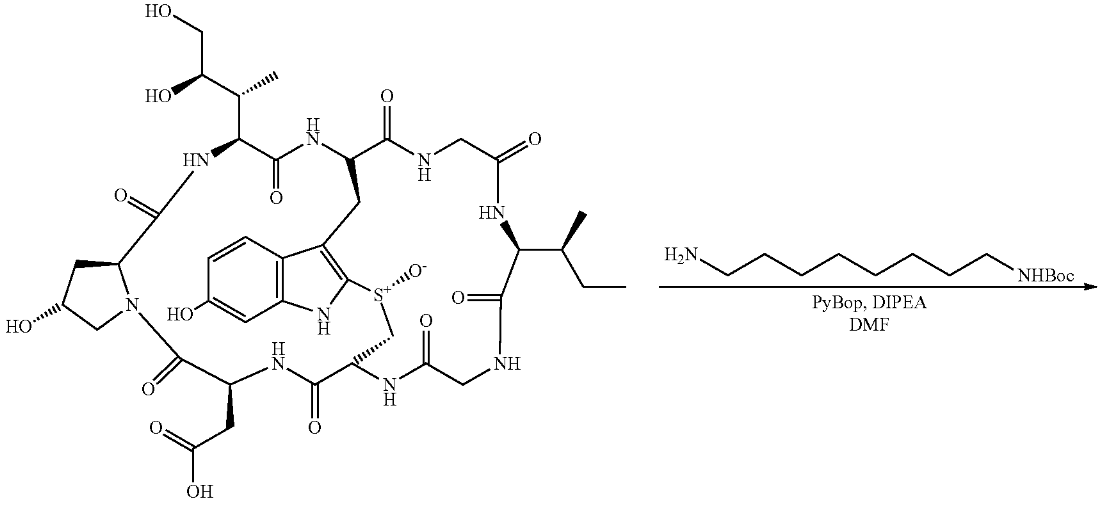

β-amanitin

-continued

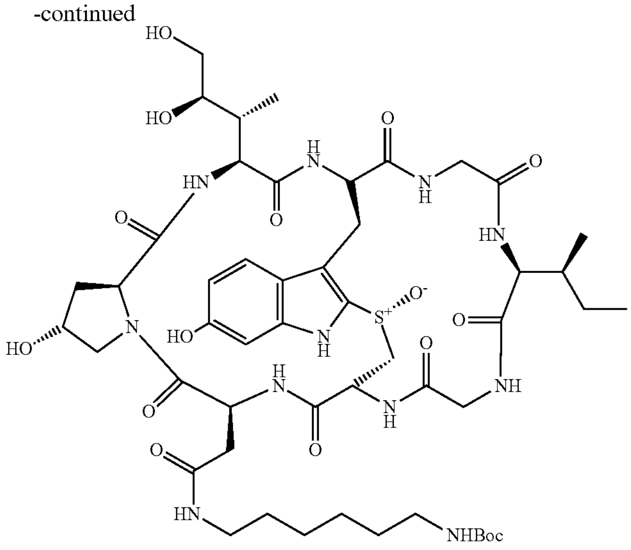

HDP 30.0299

Under argon 4.65 mg (5.05 μmol) of vacuum dried β-amanitin were dissolved in 1000 μl dry dimethylformamide (DMF). 100 μl of a 0.15 M solution of BocNH-hexamethylenediamine in DMF and 100 μl of a 0.15 M solution of diisopropylethylamine (DIPEA) in DMF were added at ambient temperature. After the final addition of 100 μl of a 0.30 M solution of benzotriazol-1-yl-oxytripyrrolidinophosphonium hexafluorophosphate (PyBOP) in DMF, the reaction mixture was stirred for 20 h and hydrolyzed with 100 μl of water. The reaction mixture was evaporated to dryness in vacuum and the residue dissolved in 1000 μl dimethylsulfoxide (DMSO). The purification was carried out on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fractions with the same retention time were collected and the solvents evaporated.

4.45 mg (80% yield) of a white solid. MS: 1119 $M+H^+$; 1141 $M+Na^+$ 3.2 6'-hexamethylenediamino-β-amanitin amide HDP 30.0304

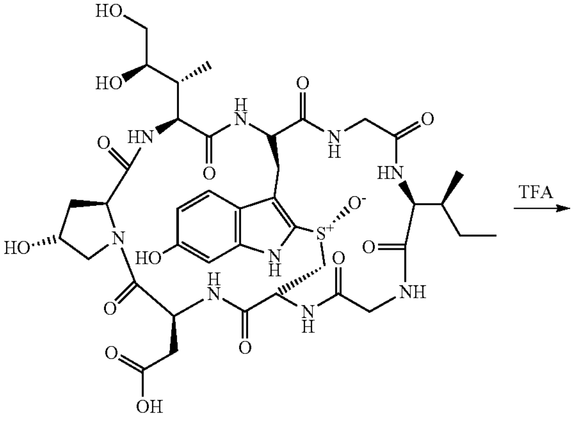

HDP 30.0299

-continued

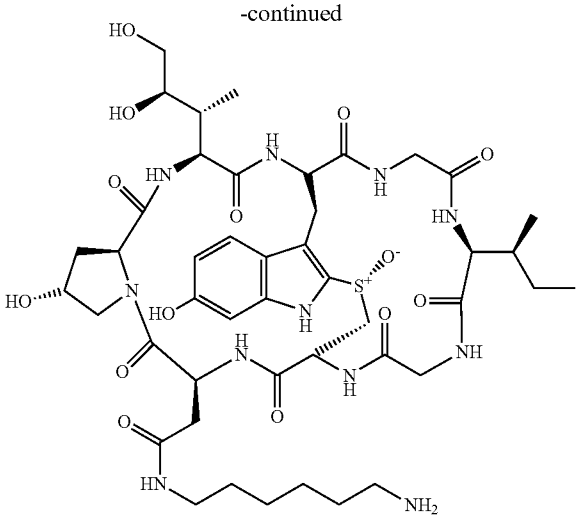

x $CF_3COOH$

HDP 30.0304

4.14 mg (3.70 μmol) BocNH-hexamethylenediamino-β-amanitin amide HDP 30.0299 were dissolved in 500 μl trifluoroacetic acid (TFA) and stirred for 2 min. The excess TFA was evaporated in vacuum and the residue co-evaporated with 2 portions of 1000 μl acetonitrile. The remaining solid was purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fractions with the same retention time 13.43-14.02 min were collected and the solvents evaporated. The residue was taken up in 2000 μl water and the solution was frozen with liquid nitrogen and freeze-dried over night.

4.00 mg (95% yield) of a white foam. MS: 1018 ($M+H^+$); 1041 ($M+Na^+$)

3.3 Synthesis of the HDP 30.0304 Antibody Derivative Her-DSC-30.0304
Scheme 3
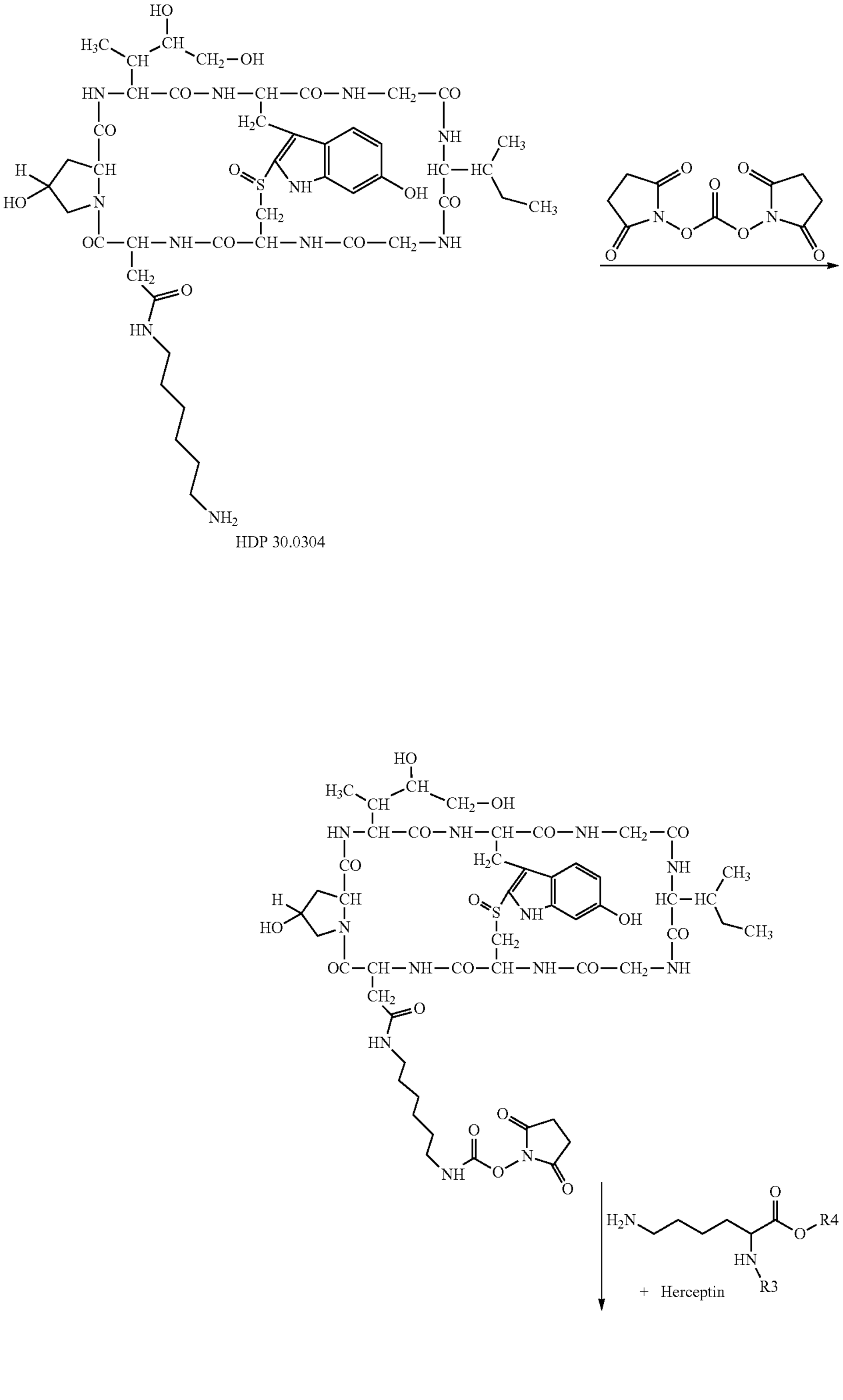
HDP 30.0304

-continued

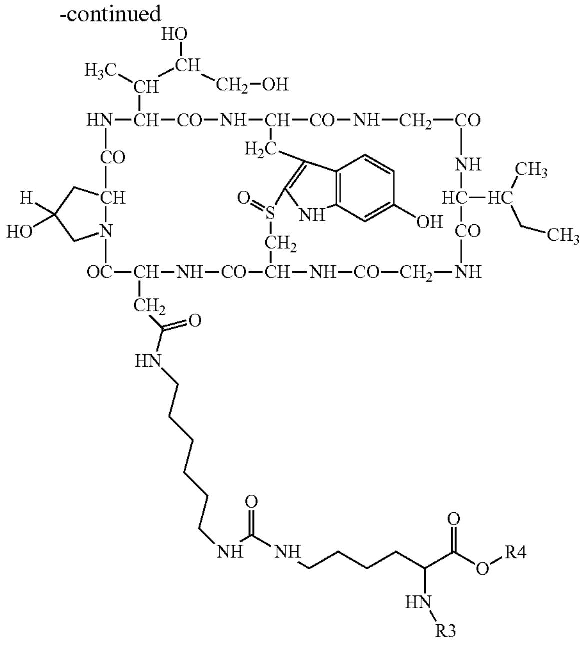

Her-DSC-30.0304

3.3.1 Synthesis of HDP-30.0304 Herceptin Conjugate Her-DSC-30.0304 [4.7]

1.33 mg HDP 30.0304 were dissolved in 144 μl dry dimethylformamide (DMF). Under argon and stirring at room temperature 13.4 μl of a solution of dihydroxysuccinimido carbonate (DSC) in DMF (2.56 mg in 100 μl DMF) and 2.6 μl triethylamine were added at once. The reaction mixture was stirred at room temperature. After 12 h, 30 ml cold diethyl ether were added. The precipitate was collected and washed several times with diethyl ether and dried in vacuum. The remaining solid was taken up in 200 μl DMF=solution A. 12.0 mg Herceptin were dissolved in 4.0 ml phosphate buffered saline (PBS, pH=7.4)=solution B. Solution A and solution B were combined. The Herceptin amanitin-linker solution was shaken at 4° C. for 14 h and separated by Sephadex G-25 gel filtration chromatography (XK-16 column; 2 ml/min). The G-25 column was prewashed with 500 ml PBS solutions, pH=7.4. The Her-DSC-30.0304 conjugate fraction was detected by UV absorption. Protein concentration was determined by RotiQuant-Assay (Carl Roth; Germany). Amanitin payload of Herceptin was determined by determination of UV absorption at A=280 nm and A=310 nm. A toxin payload of 4.7 amanitin molecules for each Herceptin molecule was calculated.

Example 4

Other Structures of Amanitin-Herceptin Conjugates

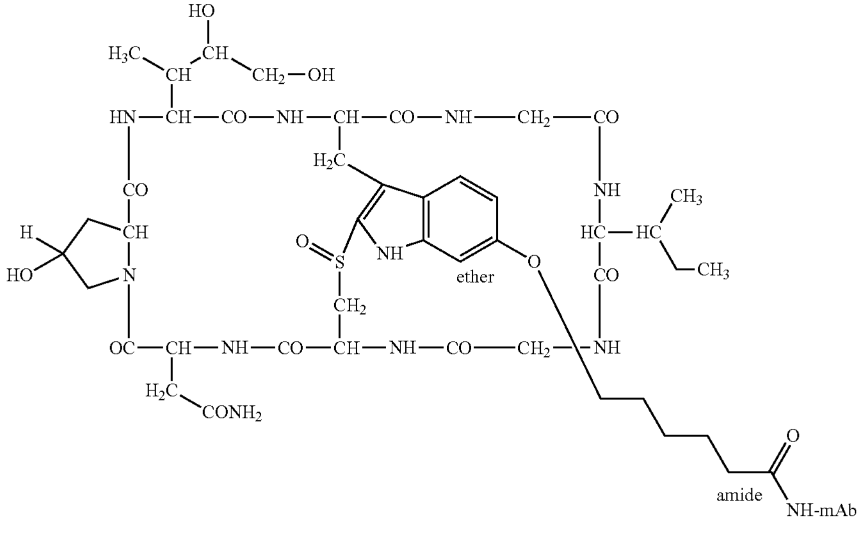

HDP mAb-DCC-30.0252

-continued
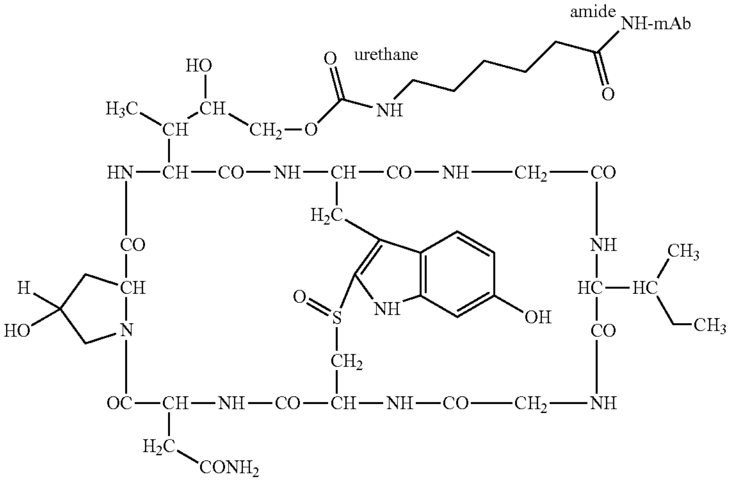
HDP mAb-DCC-30.0127
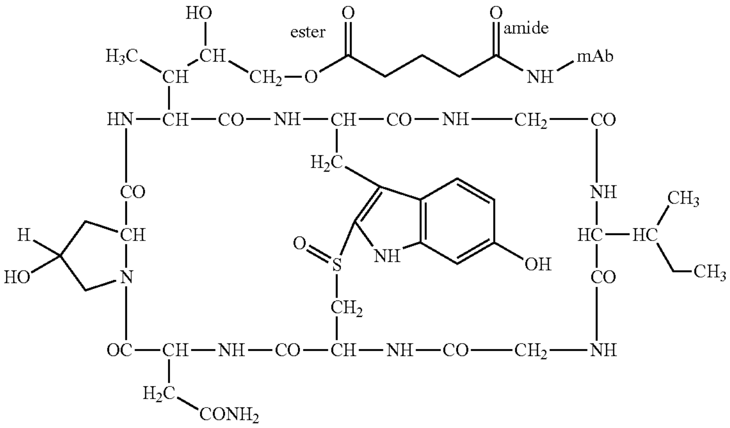
HDP mAb-Ester-30.0001
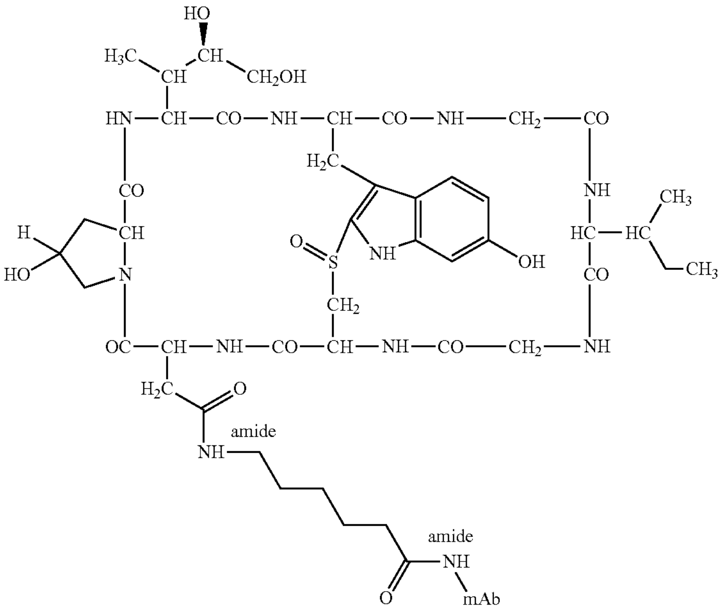
HDP mAb-DCC-30.0xyz

Example 5

Cytotoxicity of Herceptin-Amanitin Conjugates on Different HER2-Positive and HER2-Negative Tumor Cell Lines In Vitro Cytotoxic activity of Her-DSC-30.0134, Her-DSC-30.0256, Her-Ester-30.0001, Her-DCC-30.0252 and Her-DCC-30.0127 was evaluated with HER2-positive tumor cell lines SKOV-3 (ovar), SK-BR-3 (breast), NCI-N87 (stomach) and the HER2-negative tumor cell line MDA-MB231 (breast) and a chemiluminescent BrdU incorporation assay (Roche Diagnostics) in vitro. Cell viability was determined after 72 h to 96 h incubation with different concentrations of Herceptin-Amanitin conjugates at 37° C. and 5% CO2 by measurement of fixed and permealized cells with an anti-BrdU-HRP antibody in a BMG Labtech Optima microplate reader. EC50 values of dose-response curves were calculated by Graphpad Prism 4.0 software (see FIGS. 2-5).

Stability of Herceptin-Amanitin Conjugates in Plasma In Vitro

5.1 Release of Amanitin after Plasma Incubation

Figure 6:
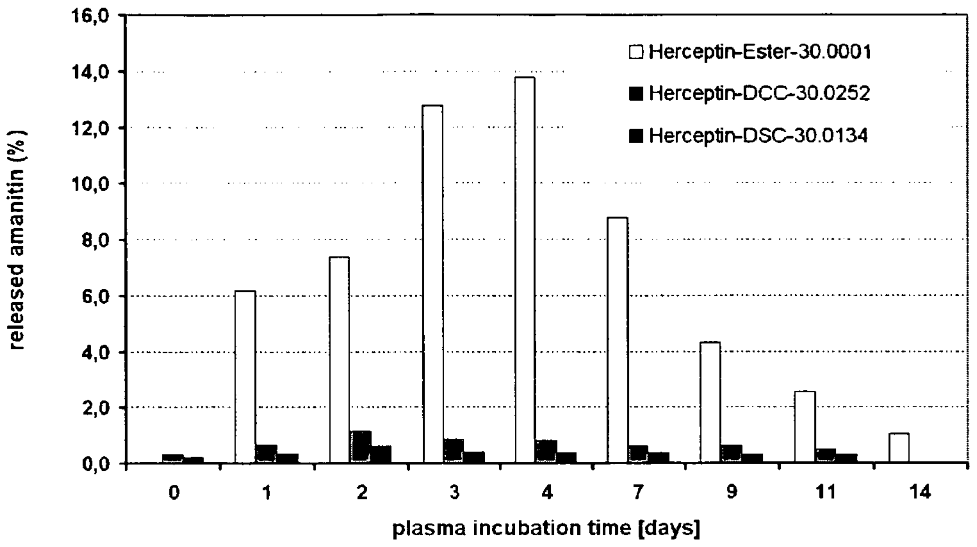
FIG. 6 and FIG. 7 show the amount of amanitin released from different amanitin herceptin conjugates using different linker moieties after incubation in plasma for up to 14 days.
Figure 7:
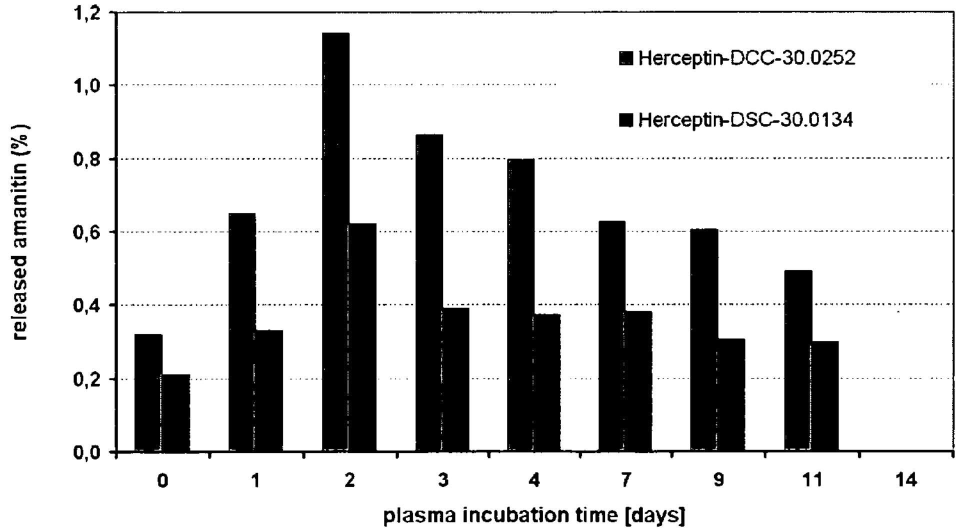

35 μM Herceptin-Amanitin conjugates were incubated for up to 14 days in mouse plasma in a water bath at 37° C. Samples were collected at different time points and analyzed for released small molecule amanitin compounds by an ELISA method. Therefor, released amanitin and amanitin metabolites were extracted at different time points with 80% EtOH. The solutions were cleared by centrifugation at 10.000 g for 5 min and the supernatants were stored at −70° C. A white Lumitrac (Greiner) microwell-plate was coated with rabbit anti-amanitin antiserum over night at 4° C. Plate was blocked with 3% BSA in PBS for 1 h at 37° C. and washed for three times with 0.05% Tween/PBS. Amanitin samples and amanitin solutions with defined concentrations were mixed with 1 nM biotinyl-amanitin in 1% BSA/PBS and incubated in coated wells for 1 h at 37° C. Wells were washed for three times with 0.05% Tween/PBS. Streptavidin-HRP (Sigma-Aldrich) stock solution (1 mg/ml in PBS) was diluted 1:1000 in 3% BSA/PBS and 50 μl were added to each well. After incubation for 1 h at 37° C., wells were washed three times with 0.05% Tween/PBS. 50 μl luminol solution (Applichem) were added to each well and luminescence signal was measured by a BMG Labtech Optima reader. Amounts of released amanitin compounds were calculated by linear regression (see FIGS. 6-7).

5.2 Cytotoxic Activity after Plasma Incubation

Figure 8:
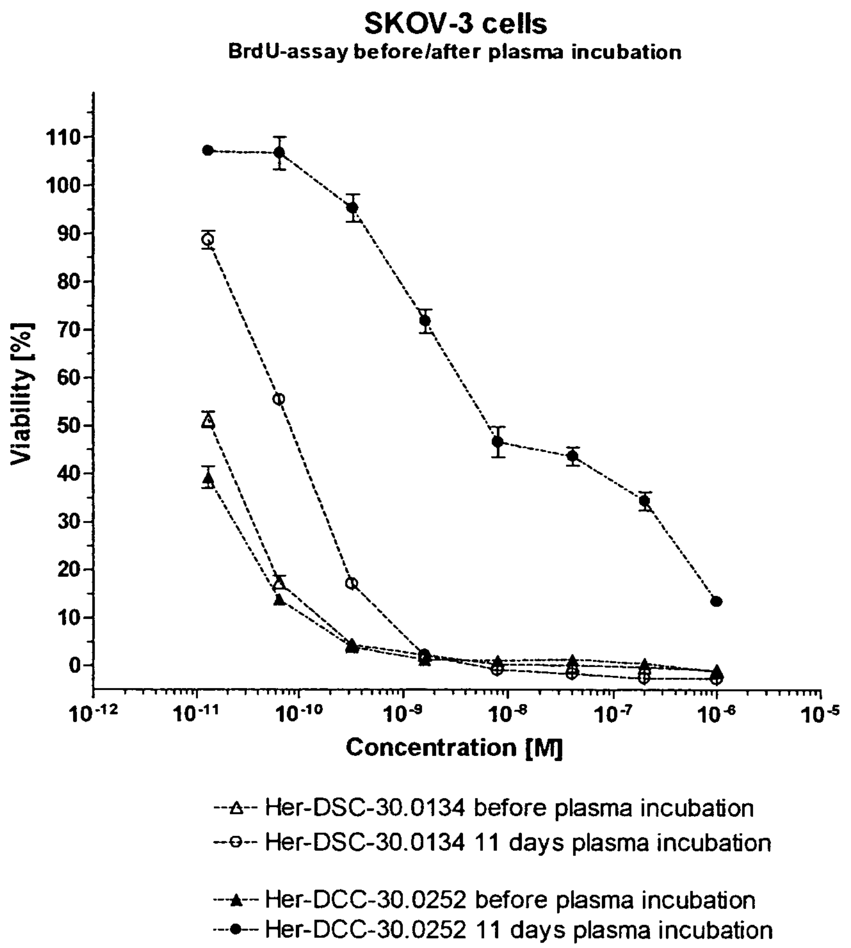
FIG. 8 shows a comparison of the cytotoxic activity of different amanitin herceptin conjugates using different linker moieties on SKOV-3 cells in a BrdU assay before and after plasma incubation.

Herceptin-Amanitin conjugates were incubated for up to 11 days in human plasma in a water bath at 37° C. Samples were collected at different time points and analyzed for remaining cytotoxic potency on HER2-positive SKOV-3 cells by a chemiluminescent BrdU incorporation assay (Roche Diagnostics) in vitro. Cell viability was determined after 72 h incubation with different concentrations of Herceptin-Amanitin conjugates at 37° C. and 5% CO2 by measurement of fixed and permealized cells with an anti-BrdU-HRP antibody in a BMG Labtech Optima microplate reader. EC50 values of dose-response curves were calculated by Graphpad Prism 4.0 software (see FIG. 8).

Figure 9:
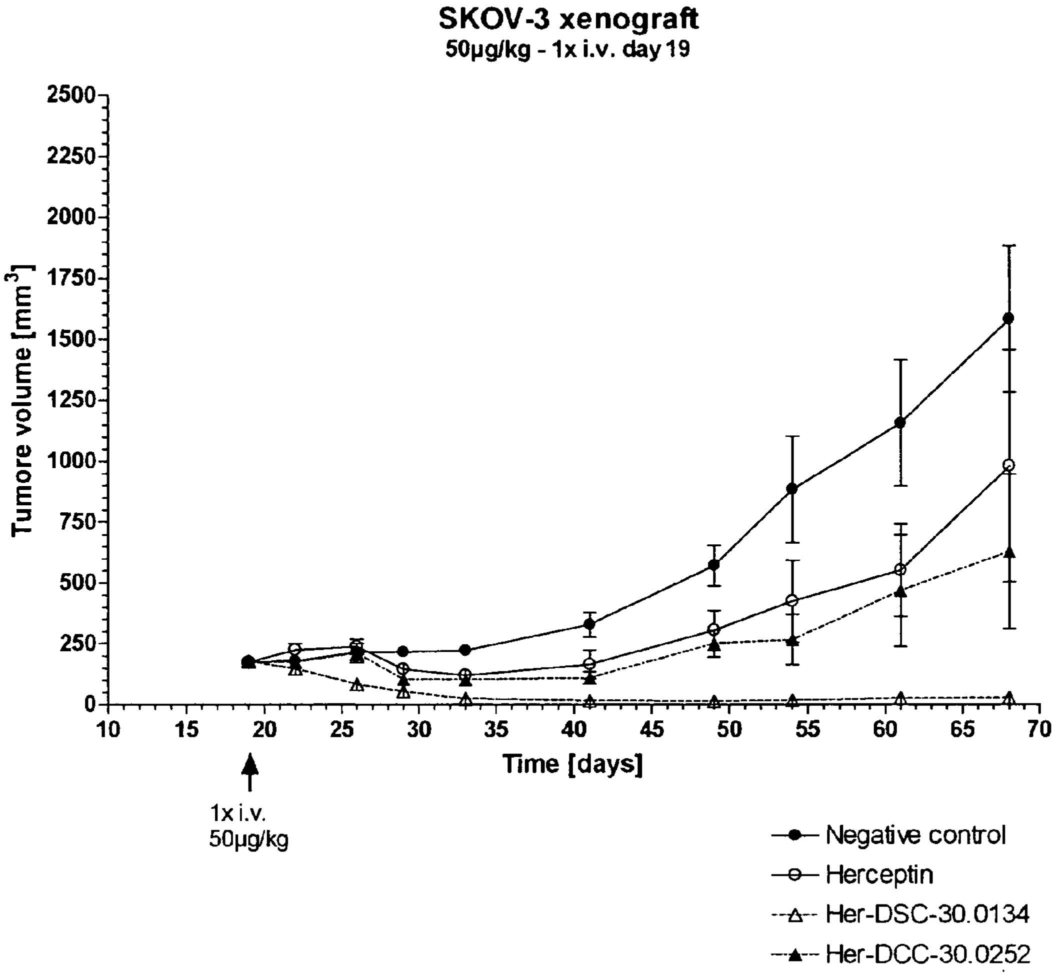
FIG. 9 shows a comparison of the activity of two different amanitin herceptin conjugates using different linker moieties in vivo in a SKOV-3 xenograft model.

Antitumoral Activity of Herceptin-Amanitin Conjugates in Mouse Xenograft Models with HER2-Positive Cancer Cells Six-week old intact female BALB/c nu/nu athymic mice were purchased (Janvier) and randomly divided into three groups of eight mice each. 2.5×106 SKOV-3 cells were injected s.c. into the flank of each mouse. The Herceptin-Amanitin conjugates were injected once i.v. at a dose of 50 μg/kg at day 19 day after tumor inocculation, whereas the negative control group was injected with vehicle (NaCl buffer). Parameters such as survival, weight and tumor size were recorded (see FIG. 9).

Example 6

Preparation of Additional α-Amanitin-Linker Compounds HDP 30.0353, HDP 30.0354, HDP 30.0355, HDP 30.0409, HDP 30.0410, HDP 30.0411 and HDP 30.0412

6.1 Amanitin-Linker HDP 30.0353

6.1.1 Synthesis of 6'O—(NH-boc-6-amino-3,4-dithia-hexyl)-α-amanitin HDP 30.0341

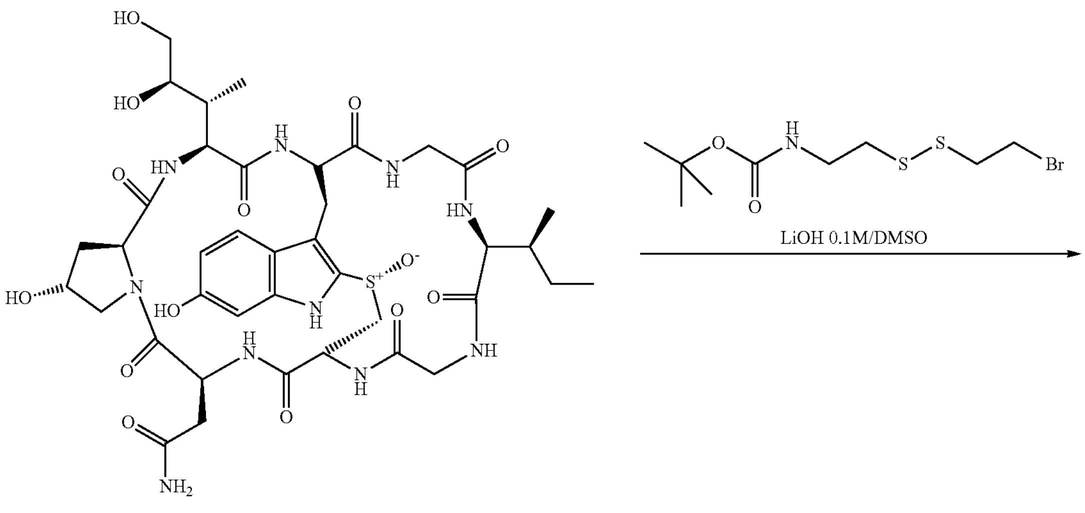

α-amanitin

-continued

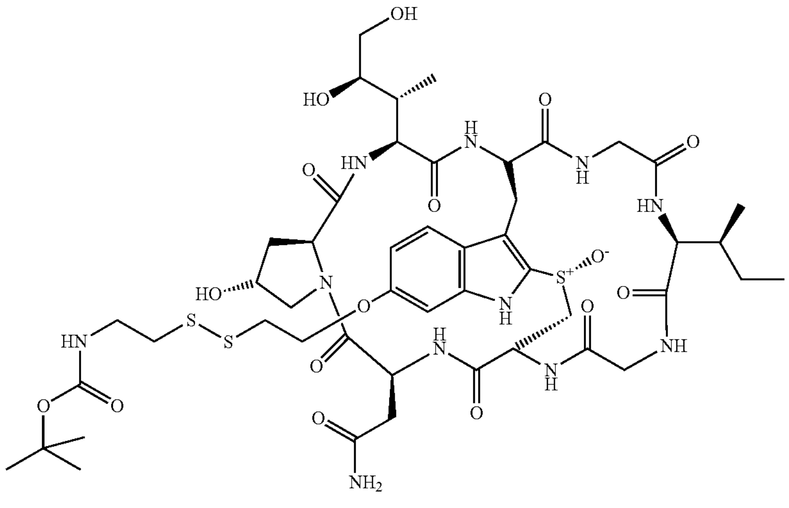

HDP 30.0341

6.78 mg (7.38 μmol) vacuum dried α-amanitin were dissolved in 500 μl dimethyl sulfoxide (DMSO). 18.67 mg (59.02 μmol, 8 eq.) NH-boc-amino-3,4-dithia-hexylbromide and 73.8 μl (7.38 μmol, 1 eq.) LiOH (0.1 M) in water/DMSO (1:1) were added under argon. After 1 h, 3.5 h, 4.5 h, 6.5 h and 8 h additional equivalents of the 0.1 M LiOH solution were added. The crude reaction mixture was purified on a LaPrep-HPLC:

column: Kromasil 100-C18, 10 μm, 250 mm×10 mm, with methanol/water (0.05% TFA), flow: 6.5 ml/min, detection at λ=295 nm. Solvent A: 95% water:5% methanol, 0.05% trifluoroacetic acid. Solvent B: 10% water:90% methanol, 0.05% trifluoroacetic acid. Gradient: 0-5 min 100% A; 5-20 min 0% A; 20-25 min 0% A; 25-27 min 100% A; 27-35 min 100% A.

The fraction with a retention time of 20.8-21.4 min was collected and the solvents evaporated in vacuum.

1.29 mg (15% yield) of a white solid. MS: 1154 M+H$^+$

6.1.2 Synthesis of 6'-O-(-6-amino-3,4-dithia-hexyl)-α-amanitin HDP 30.0353

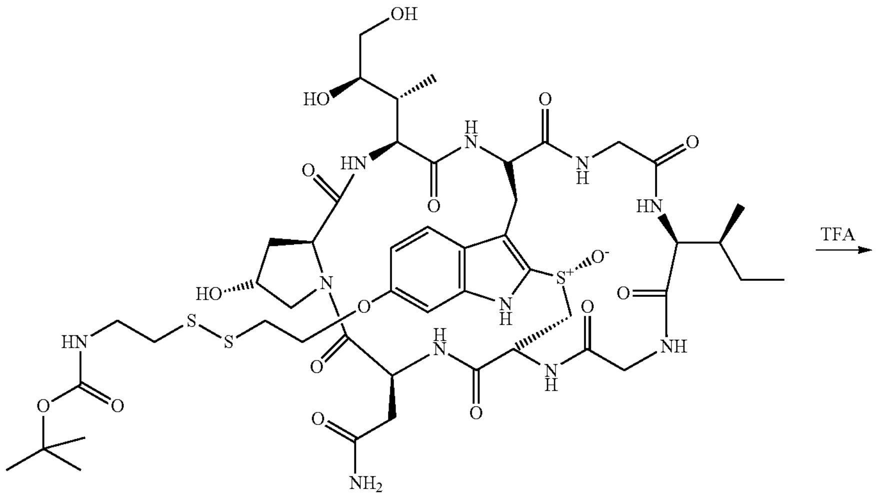

HDP 30.0341

-continued

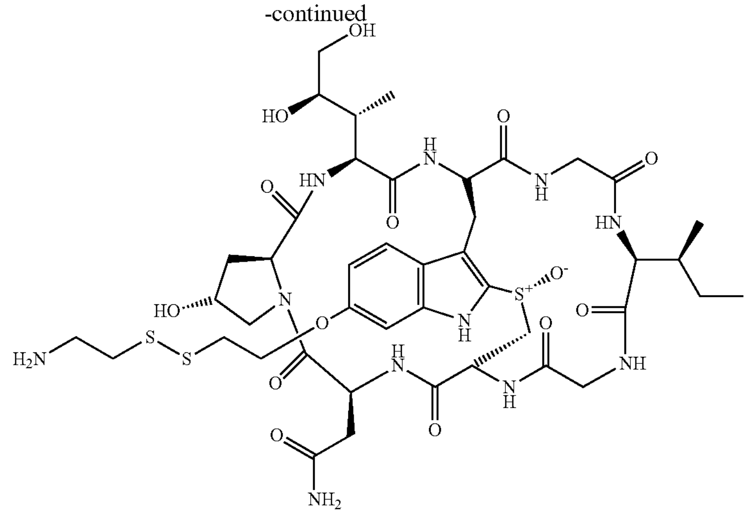

HDP 30.0353

1.29 mg (1.12 μmol) 6'-O-(−6-amino-3,4-dithia-hexyl)-α-amanitin HDP 30.0341 were dissolved in 200 μl trifluoroacetic acid (TFA). The reaction mixture was stirred under argon at ambient temperature. After 1 min the trifluoroacetic acid was diluted with 1000 μl toluene and evaporated to dryness. The temperature should not exceed 20° C. This process was repeated with 1000 μl toluene and 1000 μl acetonitrile (2×). The crude α-amanitin ether was purified on a LaPrep-HPLC:

column: Kromasil 100-C18, 10 μm, 250 mm×10 mm, with methanol/water (0.05% TFA), flow: 6.5 ml/min, detection at λ=295 nm. Solvent A: 95% water:5% methanol, 0.05% trifluoroacetic acid. Solvent B: 10% water:90% methanol, 0.05% trifluoroacetic acid. Gradient: 0-5 min 100% A; 5-25 min 50% A; 25-30 min 0% A; 30-35 min 0% A; 35-40 min 100% A, 40-45 min 100% A.

The fraction with a retention time of 16.1-17.0 min was collected and the solvents evaporated. The residue was freeze dried in water.

0.39 mg (30% yield, TFA salt) of a yellow solid. MS: 1054 $M+H^+$

6.2 Amanitin-Linker HDP 30.0354

6.2.1 Synthesis of 6'O—(NH-boc-7-amino-4,5-dithia-heptyl)-α-amanitin HDP 30.0349

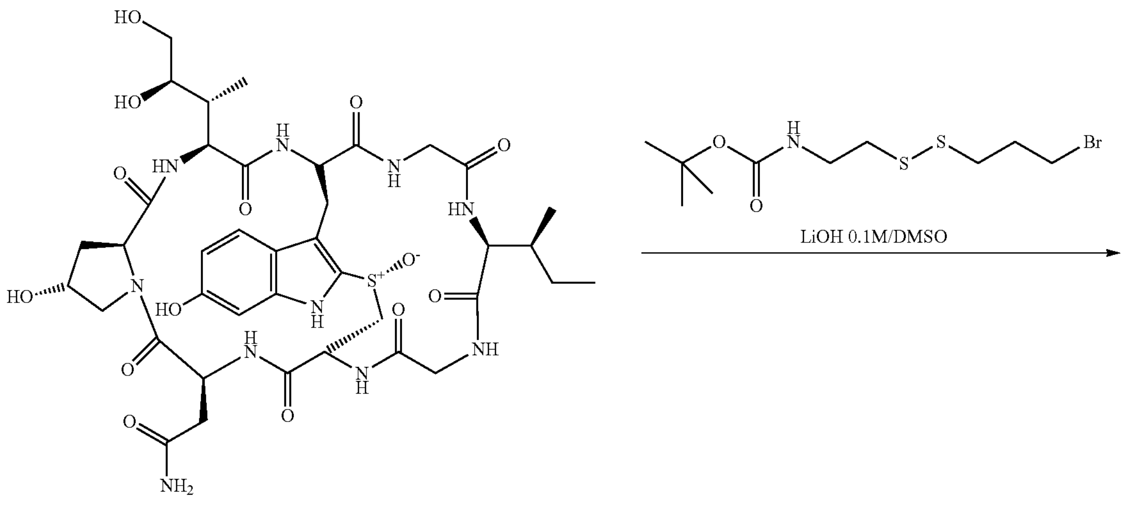

α-amanitin

-continued

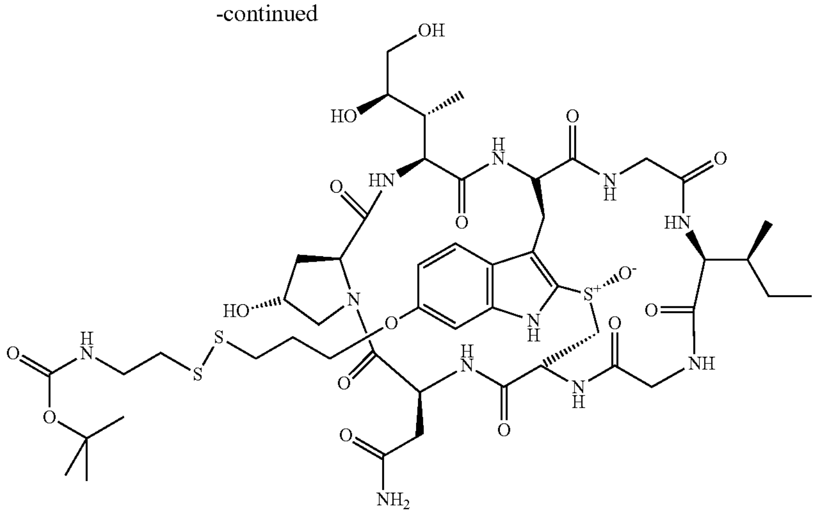

HDP 30.0349

5.67 mg (6.17 μmol) vacuum dried α-amanitin were dissolved in 250 μl dry dimethyl sulfoxide (DMSO). 19.00 mg (58.00 μmol. 9.3 eq.) of NH-boc-7-amino-4,5-dithia-heptylbromide HDP 30.0345 were added at room temperature under an atmosphere of argon. 61.7 μl (6.10 μmol, 1 eq.) 0.1 M LiOH in water/DMSO (1:1) were added at once. The reaction mixture was stirred for 3.5 h and additional 10 μl (13.00 mg; 39.7 μmol; 6.3 eq.) NH-boc-7-amino-4,5-dithia-heptylbromide HDP 30.0345 and 61.7 μl 0.1 M LiOH in water/DMSO (1:1) were added. After 8 h the crude reaction mixture was purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol, 0.05% trifluoroacetic acid. Solvent B: 10% water:90% methanol, 0.05% trifluoroacetic acid. Gradient: 0-5 min 100% A; 5-20 min 0% A; 20-30 min 0% A; 30-35 min 100% A; 35-40 min 100% A.

The fraction with a retention time of 19.4-21.0 min was collected and evaporated to dryness at room temperature.

4.83 mg (67% yield) of a white powder. MS: 1168 M+H$^+$ 6.2.2 Synthesis of 6'O-(7-amino-4,5-dithia-heptyl)-α-amanitin HDP 30.0354

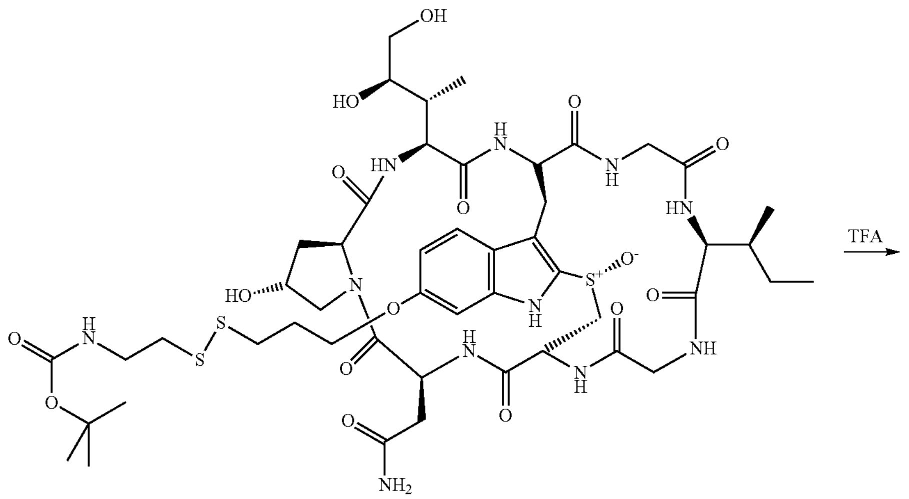

HDP 30.0349

-continued

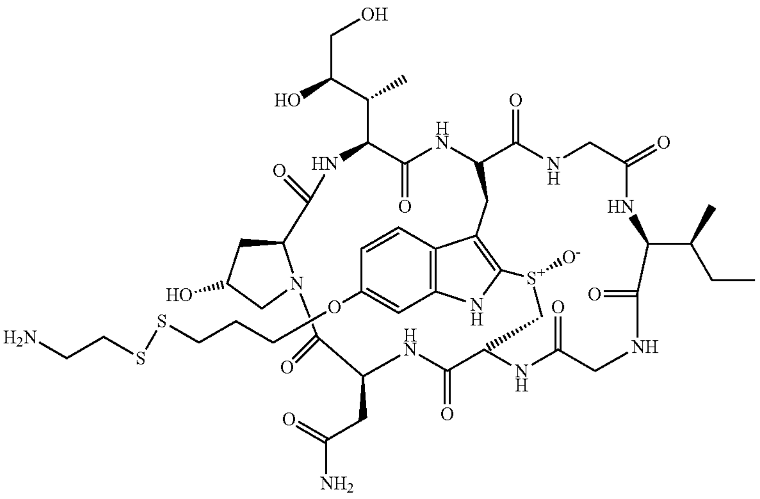

HDP 30.0354

4.83 mg (4.13 μmol) 6'O—(NH-boc-7-amino-4,5-dithia-heptyl)-α-amanitin HDP 30.0349 were dissolved in 200 μl trifluoroacetic acid (TFA). The reaction mixture was stirred for 1 min under argon and evaporated to dryness at ambient temperature. The residue was co-evaporated with 1000 μl toluene and 1000 μl acetonitrile. The remaining solid was purified on a LaPrep-HPLC:

column: Kromasil 100-C18, 10 μm, 250 mm×10 mm, with methanol/water (0.05% TFA), flow: 6.5 ml/min, detection at λ=295 nm. Solvent A: 95% water:5% methanol, 0.05% trifluoroacetic acid. Solvent B: 10% water:90% methanol, 0.05% trifluoroacetic acid. Gradient: 0-5 min 100% A; 5-20 min 0% A; 20-25 min 0% A; 25-27 min 100% A; 27-35 min 100% A.

The fraction with a retention time of 17.1-17.5 min was collected and evaporated. The residue was freeze dried in water.

0.36 mg (7.0% yield, TFA salt) of a yellow solid. MS: 1068 $M+H^+$

6.3 Amanitin-Linker HDP 30.0355

6.3.1 Synthesis of 6'O—(NH-boc-7-amino-3,3-dimethyl-4,5-dithia-heptyl)-α-amanitin HDP 30.0350

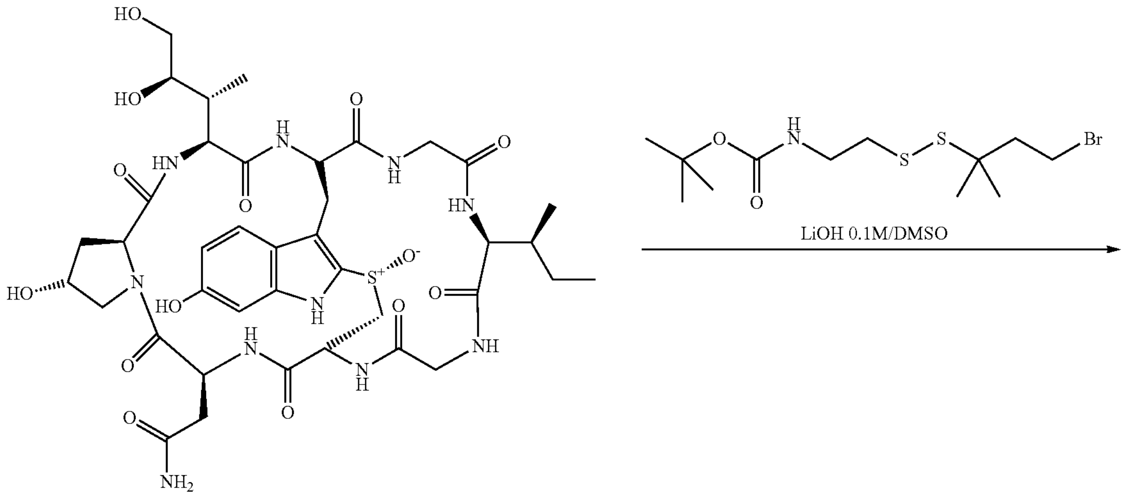

α-amanitin

-continued

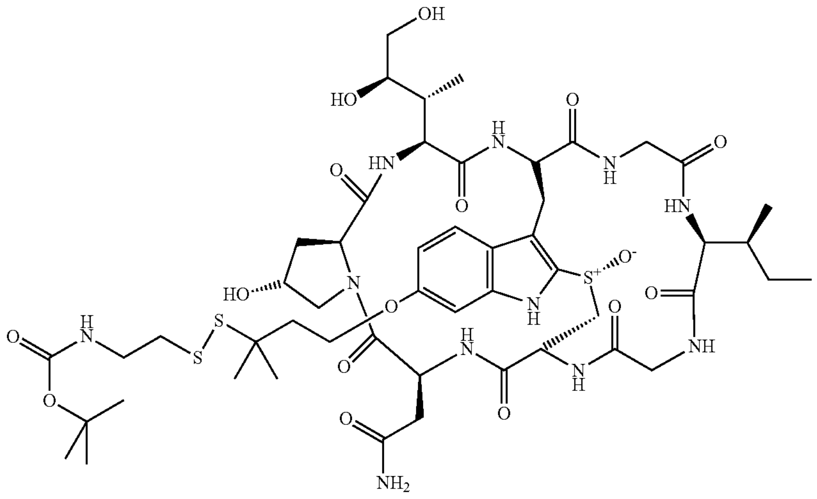

HDP 30.0350

5.67 mg (6.17 μmol) vacuum dried α-amanitin were dissolved in 250 μl dry dimethyl sulfoxide (DMSO). Under argon 18.00 mg (51.62 μmol, 9.8 eq.) NH-boc-7-amino-3,3-dimethyl-4,5-dithia-heptylbromide HDP 30.0348 and 61.7 μl (6.10 μmol, 1 eq.) 0.1 M LiOH in water/DMSO (1:1) were added. After 2 h the reaction mixture was repeatedly treated with 10 μl (12.00 mg; 34.4 μmol; 5.6 eq.) NH-boc-7-amino-3,3-dimethyl-4,5-dithia-heptylbromide HDP 30.0345 and 61.7 μl 0.1 M LiOH. After 8 h the mixture was diluted with DMSO and purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol, 0.05% trifluoroacetic acid. Solvent B: 10% water:90% methanol, 0.05% trifluoroacetic acid. Gradient: 0-5 min 100% A; 5-20 min 0% A; 20-30 min 0% A; 30-35 min 100% A; 35-40 min 100% A.

The fraction with a retention time of 20.5-21.0 min was collected and the solvents evaporated.

0.51 mg (7% yield; 48% yield based on converted α-amanitin). MS: 1196 $M+H^+$

6.3.2 Synthesis of 6'O-(7-amino-3,3-dimethyl-4,5-dithia-heptyl)-α-amanitin HDP 30.0355

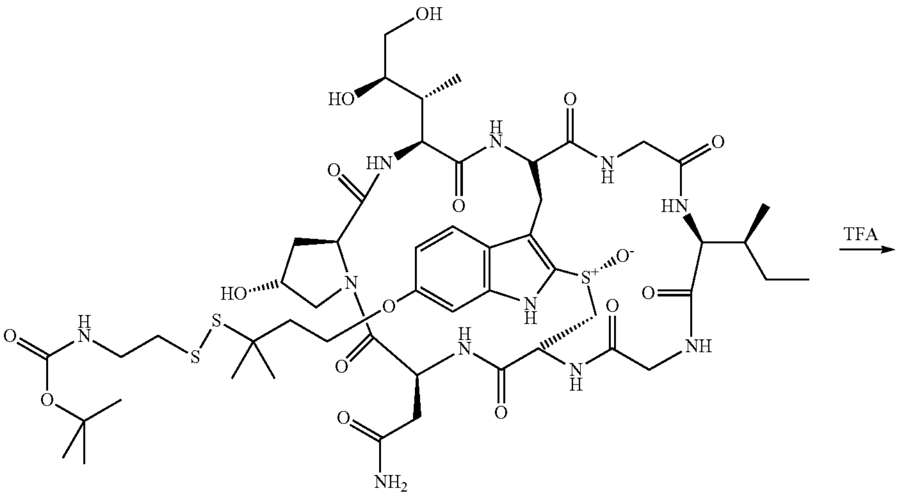

HDP 30.0350

-continued

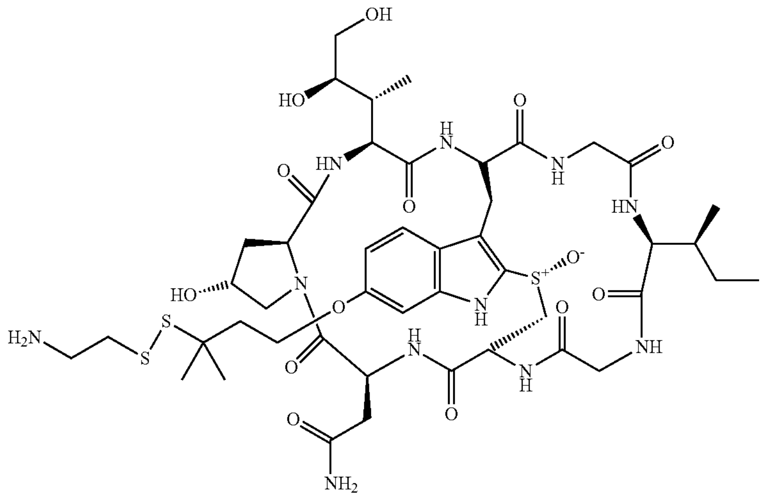

HDP 30.0355

0.51 mg (0.43 μmol) HDP 30.0350 were dissolved in 200 μl trifluoroacetic acid (TFA) and stirred for 1 min at ambient temperature. The trifluoroacetic acid was diluted with 1000 μl toluene and evaporated at 20° C. to dryness. This process was repeated with 1000 μl toluene and 1000 μl acetonitrile (2×). The reaction mixture was purified on a LaPrep-HPLC:

column: Kromasil 100-C18, 10 μm, 250 mm×10 mm, with methanol/water (0.05% TFA), flow: 6.5 ml/min, detection at λ=295 nm. Solvent A: 95% water:5% methanol, 0.05% trifluoroacetic acid. Solvent B: 10% water:90% methanol, 0.05% trifluoroacetic acid. Gradient: 0-5 min 100% A; 5-20 min 0% A; 20-25 min 0% A; 25-27 min 100% A; 27-35 min 100% A.

The fraction with a retention time of 18.2-18.6 min was collected and the solvents evaporated. The residue was freeze dried in water.

0.15 mg (27% yield, TFA salt) of a yellow solid. MS: 1096 $M+H^+$ 6.4 Amanitin-Linker HDP 30.0409

6.4.1 Synthesis of 6'O—(NH-boc-12-amino-dodecyl)-α-amanitin HDP 30.0404

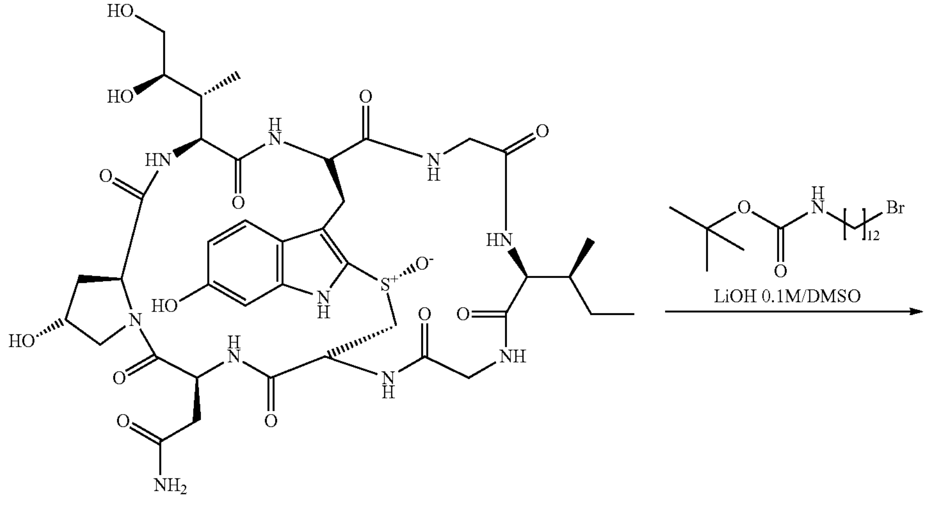

α-amanitin

-continued

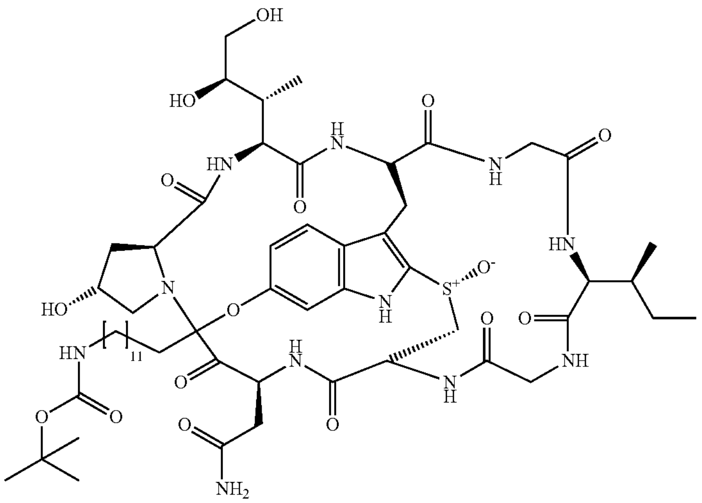

HDP 30.0404

6.67 mg (7.26 μmol) vacuum dried α-amanitin were dissolved in 250 μl dry dimethyl sulfoxide (DMSO). 21.00 mg (58.10 μmol, 8 eq.) NH-boc-12-amino-dodecylbromide HDP 30.0383 and 72.6 μl (7.26 μmol, 1 eq.) 0.1 M LiOH in water/DMSO (1:1) were added. After 6 h 36.5 μl 0.1 M LiOH were added and the mixture quenched with 72.6 μl of a 0.1 M acetic acid solution in DMSO two h later. The crude reaction product was purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time of 22.0-22.7 min was collected and the solvents evaporated.

5.96 mg (68% yield) of a white solid. MS: 1202 M+H$^+$

6.4.2 Synthesis of 6'-O-(12-aminododecyl)-α-amanitin HDP 30.0409

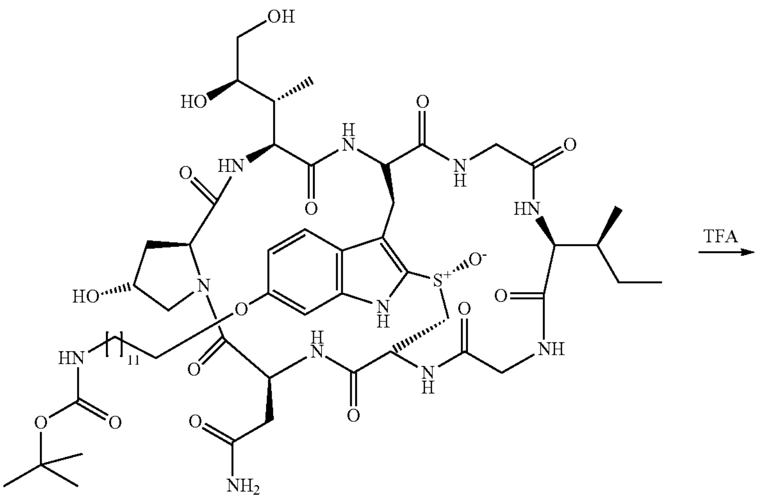

HDP 30.0404

-continued

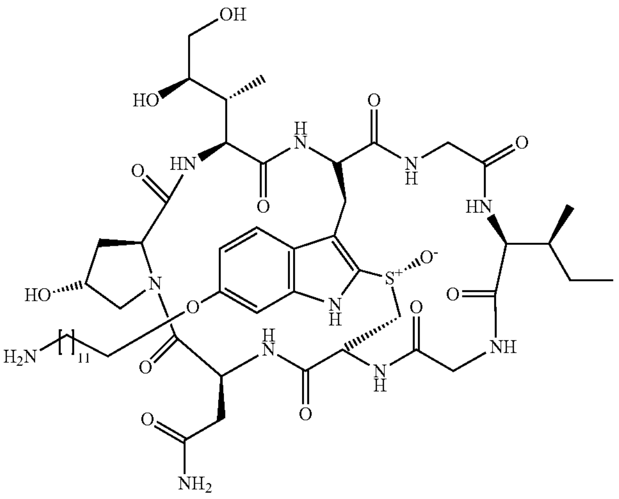

HDP 30.0409

5.96 mg (4.96 μmol) HDP 30.0404 were dissolved in 200 μl trifluoroacetic acid (TFA) and stirred 1 min at ambient temperature. The reaction mixture was co-evaporated with 1000 μl toluene and acetonitrile and the remaining solid purified on a LaPrep-HPLC:

column: Kromasil 100-C18, 10 μm, 250 mm×20 mm, with acetonitrile/water, flow: 26 ml/min, detection at λ=295 nm. Solvent A: 95% water:5% acetonitrile. Solvent B: 5% water:95% acetonitrile. Gradient: 0-5 min 100% A; 5-20 min 0% A; 20-25 min 0% A; 25-27 min 100% A; 27-35 min 100% A.

The fraction with a retention time between 18.6-19.2 min was collected and evaporated to a white solid.

6.03 mg (99% yield, TFA salt). MS: 1102 M+H$^+$

6.5 Amanitin-Linker HDP 30.0410

6.5.1 Synthesis of 6'O—(NH-boc-11-amino-3,6,9-trioxa-undecyl)-α-amanitin HDP 30.0405

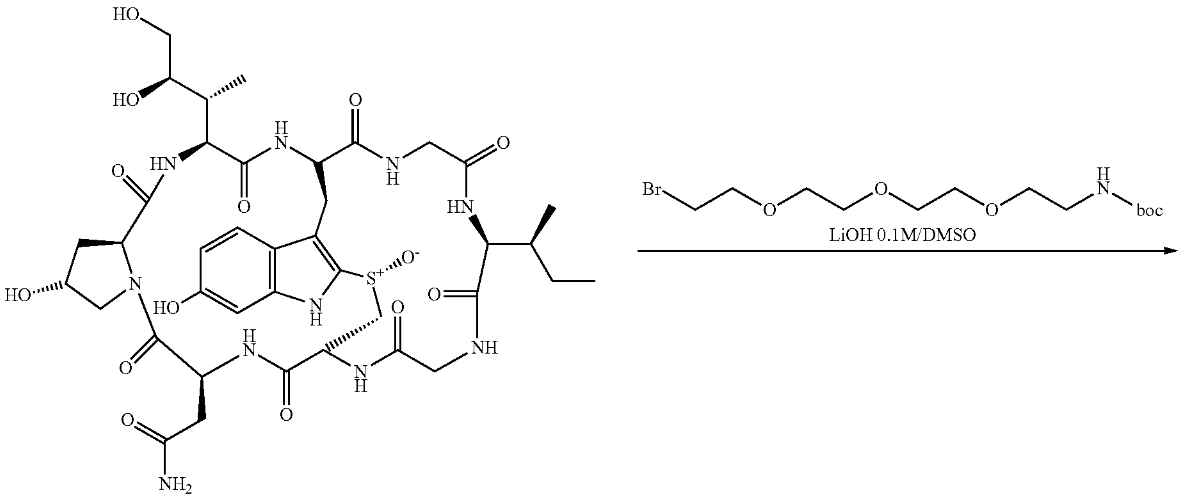

α-amanitin

-continued

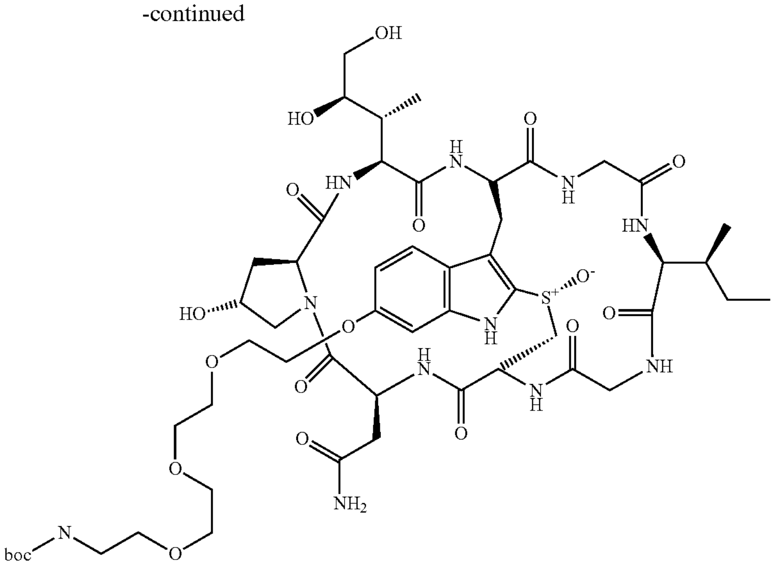

HDP 30.0405

6.67 mg (7.26 μmol) vacuum dried α-amanitin were dissolved in 250 μl dry dimethyl sulfoxide (DMSO). 20.51 mg (58.10 μmol, 8 eq.) NH-boc-11-amino-3,6,9-trioxa-undecyl-bromide HDP 30.0391 and 72.6 μl (7.26 μmol, 1 eq.) 0.1 M LiOH in water/DMSO (1:1) were added. The reaction was carried out at ambient temperature under an atmosphere of argon. After 6 h additional LiOH base (0.5 eq.) was added. The mixture was quenched after 8 h with 72.6 μl of a 0.1 M acetic acid solution in DMSO and purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time of 18.1-18.6 min was collected and the solvents evaporated.

4.68 mg (54% yield) of solid. MS: 1194 M+H$^+$ 6.5.2 Synthesis of 6'O-(11-amino-3,6,9-trioxa-undecyl)-α-amanitin HDP 30.0410

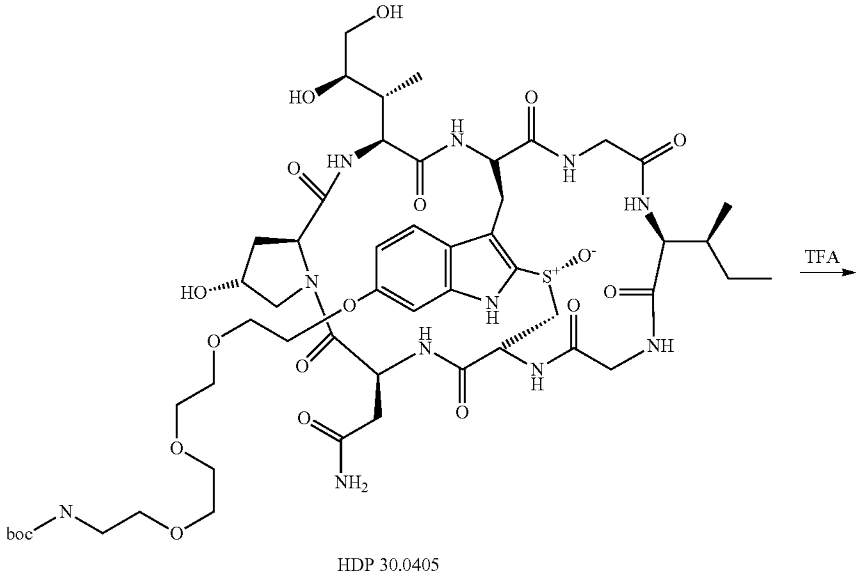

HDP 30.0405

-continued

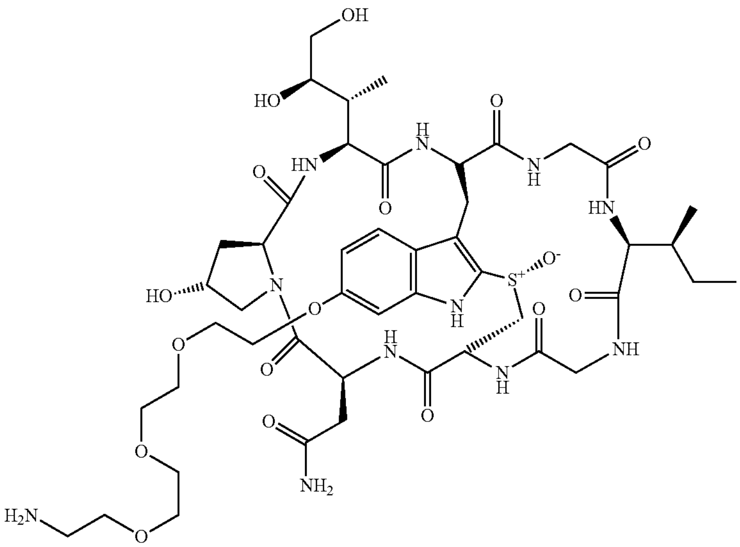

HDP 30.0410

4.68 mg (3.92 μmol) HDP 30.0405 were dissolved in 200 μl trifluoroacetic acid (TFA) and stirred for 1 min at ambient temperature. The reaction mixture was co-evaporated with toluene and acetonitrile and the crude solid purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time between 18.6-19.2 min was collected and evaporated. The remaining solid was freeze dried in water.

2.44 mg (52% yield, TFA salt). White powder MS: 1102 $M+H^+$

6.6 Amanitin-Linker HDP 30.0411

6.6.1 Synthesis of 6'O—(NH-boc-16-amino-hexadecyl)-α-amanitin HDP 30.0406

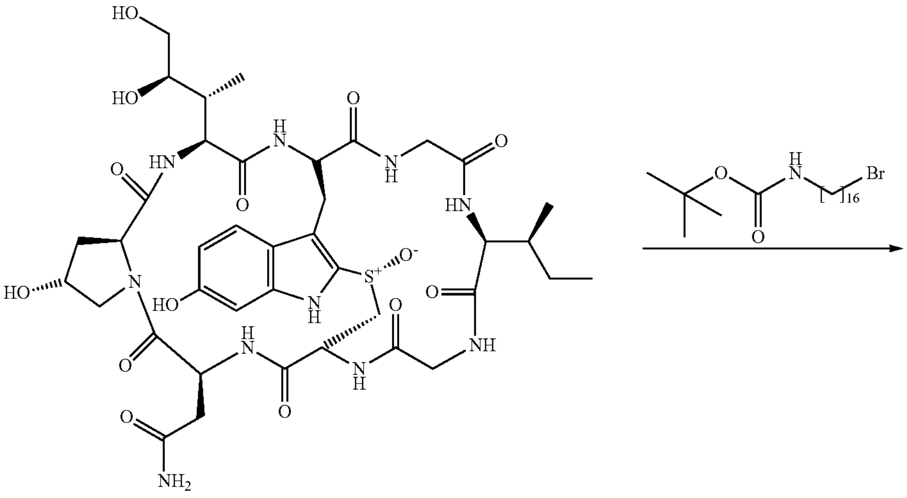

α-amanitin

-continued

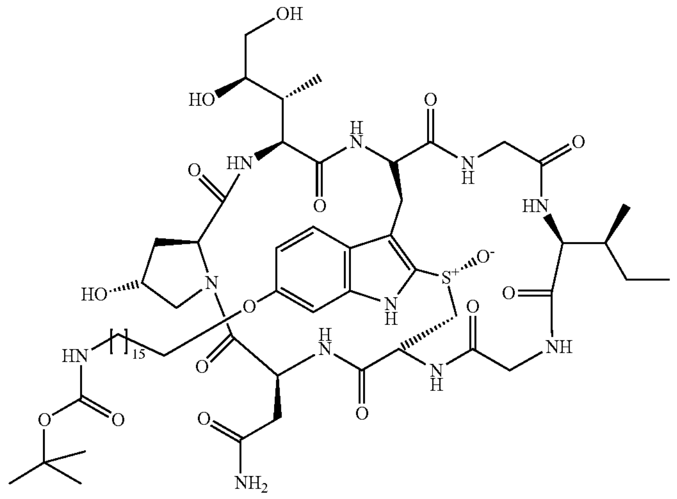

HDP 30.0406

6.67 mg (7.26 μmol) vacuum dried α-amanitin were dissolved in 750 μl dry dimethyl sulfoxide (DMSO). 24.00 mg (58.10 μmol, 8 eq.) NH-boc-16-amino-hexadecylbromide HDP 30.0398 were added at room temperature under argon. 72.6 μl (7.26 μmol, 1 eq.) 0.1 M LiOH in water/DMSO (1:1) were added and the reaction mixture heated to 50° C. After 6 h additional LiOH base (36.5 μl) was added and the reaction mixture quenched after of 8 h with 72.6 μl of a 0.1 M acetic acid solution in DMSO. The solidified reaction mixture was diluted with DMSO and purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time of 23.4-24.1 min was collected and the solvents evaporated.

4.41 mg (48% yield) of a white solid. MS: 1258 M+H$^+$ 6.6.2 Synthesis of 6'O-(16-amino-hexadecyl)-α-amanitin HDP 30.0411

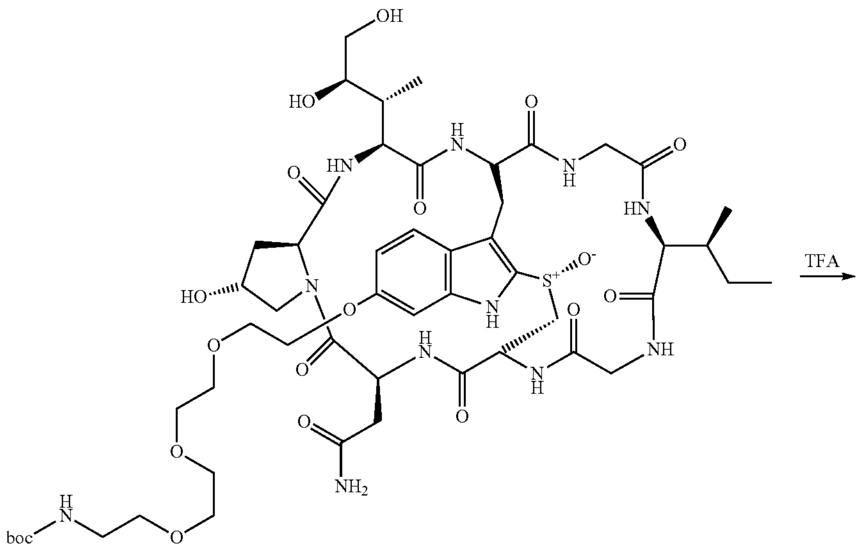

HDP 30.0406

-continued

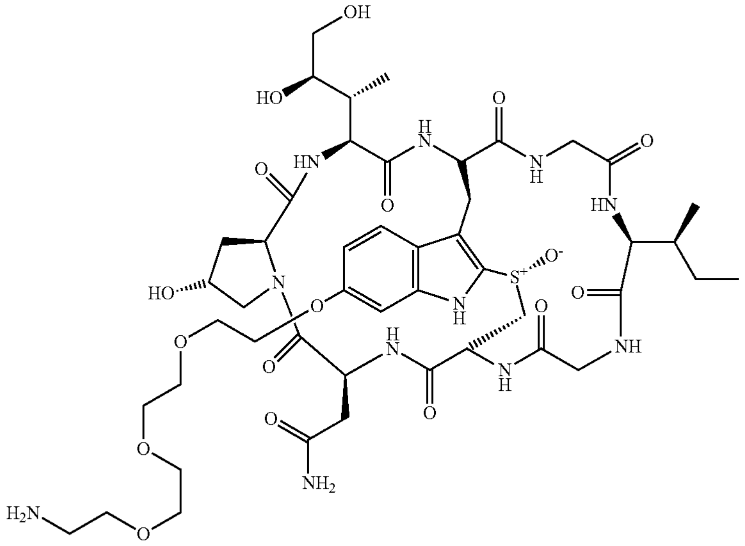

HDP 30.0411

4.41 mg (3.50 μmol) HDP 30.0406 were dissolved in 200 μl trifluoroacetic acid (TFA) and stirred for 2 mins at ambient temperature. The reaction mixture was co-evaporated two times with 1000 μl toluene and 1000 μl acetonitrile and the solid residue purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time between 20.5-21.2 min was collected and evaporated. The residue was freeze dried in water.

2.44 mg (52% yield, TFA salt). MS: 1102 $M+H^+$

6.7 Amanitin-Linker HDP 30.0412

6.7.1 Synthesis of 6'O—(NH-boc-2-amino-ethyl)-α-amanitin HDP 30.0317

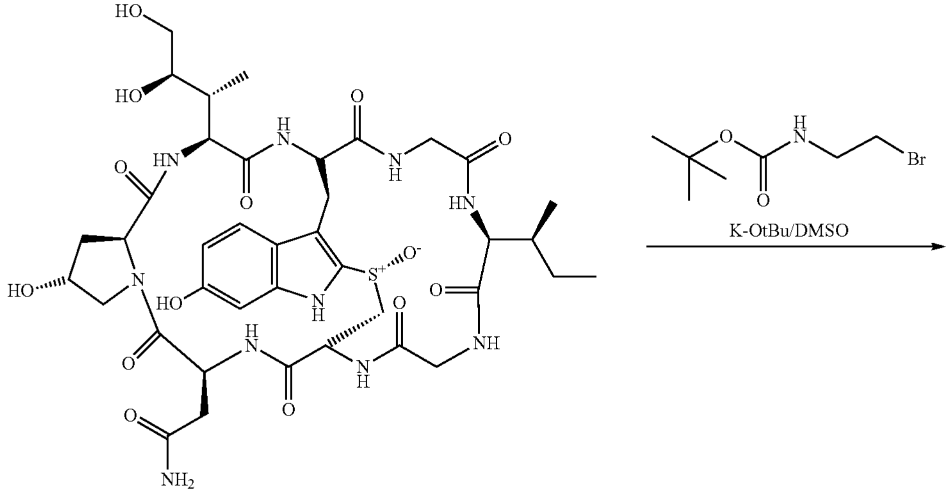

α-amanitin

-continued

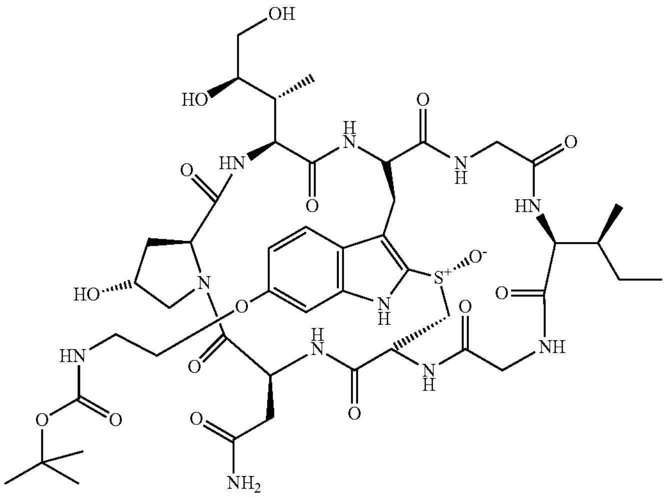

HDP 30.0317

20.00 mg (21.8 μmol) vacuum dried α-amanitin were dissolved in 900 μl dry dimethyl sulfoxide (DMSO). 100.0 μl (21.8 μmol, 1 eq.) of a 0.218M solution of potassium-t-butylate in DMSO and 39.00 mg (174.1 μmol, 8 eq.) NH-boc-2-aminoethylbromide (obtained from Fluka) were added at room temperature. After 4 and 6 h 1 and 2 additional equivalents of potassium-t-butylate and NH-boc-2-aminoethylbromide were added. The mixture was quenched after 23 h with 72.6 μl of a 0.1 M acetic acid solution in DMSO and purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time between 13.2-14.5 min was collected and the solvents evaporated.

3.86 mg (16% yield) of a white solid. MS: 1062 M+H$^+$ 6.7.2 Synthesis of 6'O-(2-amino-ethyl)-α-amanitin HDP 30.0412

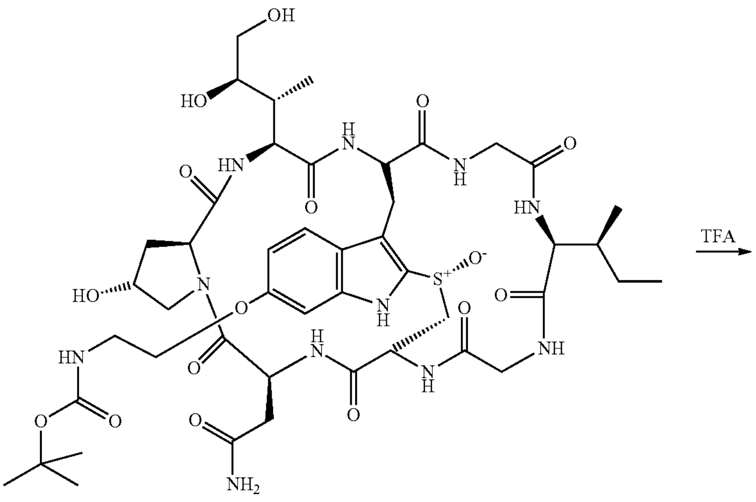

HDP 30.0317

-continued

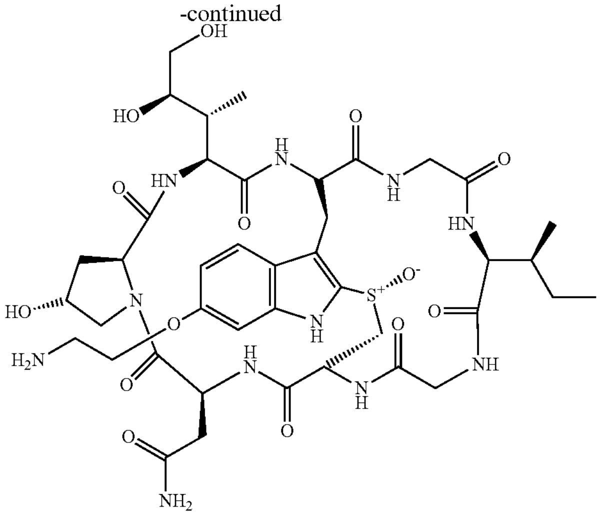

HDP 30.0412

3.86 mg (3.36 μmol) HDP 30.0317 were dissolved in 200 μl trifluoroacetic acid (TFA) and stirred for 2 mins at room temperature. The reaction mixture was co-evaporated with 1000 μl toluene and 1000 μl acetonitrile and the solid purified on a LaPrep-HPLC:

column: Kromasil 100-C18, 10 μm, 250 mm×20 mm, with methanol/water (0.05% TFA), flow: 26 ml/min, detection at λ=295 nm. Solvent A: 95% water:5% methanol. Solvent B: 5% water:95% methanol. Gradient: 0-5 min 100% A; 5-20 min 0% A; 20-25 min 0% A; 25-27 min 100% A; 27-35 min 100% A.

The fraction with a retention time between 20.5-21.2 min was collected and evaporated. The residue was freeze dried in water.

1.54 mg (44% yield, TFA salt) of a white solid. MS: 962 M+H$^+$

The invention claimed is:

1. A conjugate comprising a target-binding moiety linked via a linker L to an amatoxin, wherein the linker L is connected to the amatoxin via (i) the γ C-atom of amatoxin amino acid 1, particularly via an amide linkage;

(ii) an oxygen atom bound to the δ C-atom of amatoxin amino acid 3, particularly via an ester linkage, an ether linkage or a urethane linkage; or (iii) the 6' C-atom of amatoxin amino acid 4, particularly via an oxygen atom bound to the 6' C-atom of amatoxin amino acid 4; in each case wherein the linker L is connected to the target-binding moiety via a urea moiety.

2. The conjugate of claim 1, wherein the conjugate has a structure selected from one of the following structures:

(i) amatoxin-γC(O)—NH-L-NH—C(O)—NH-target-binding moiety;

(ii) amatoxin-δC-O—C(O)-L-NH—C(O)—NH-target-binding moiety;

(iii) amatoxin-δC-O-L-NH—C(O)—NH-target-binding moiety;

(iv) amatoxin-δC-O—C(O)—NH-L-NH—C(O)—NH-target-binding moiety; and (v) amatoxin-6'C—O-L-NH—C(O)—NH-target-binding moiety.

3. The conjugate of claim 1, wherein the target-binding moiety is connected to the linker L via an amino group present in the target-binding moiety, wherein said amino group forms part of said urea moiety.

4. The conjugate of claim 1, wherein the amatoxin is selected from α-amanitin, β-amanitin, γ-amanitin, ε-amanitin, amanin, amaninamide, amanullin, or amanullinic acid, or from salts or analogues thereof.

5. The conjugate of claim 1, wherein the linker L is an alkylene, heteroalkylene, alkenylene, heteroalkenylene, alkynylene, heteroalkynylene, cycloalkylene, heterocycloalkylene, arylene, heteroarylene, aralkylene, or a heteroaralkylene group, optionally substituted.

6. The conjugate of claim 1, wherein the linker L comprises a moiety selected from one of the following moieties: a disulfide, an ether, an amine, an ester, a carboxamide, a urethane, and a urea moiety.

7. The conjugate of claim 1, wherein the target-binding moiety specifically binds to an epitope that is present on a tumour cell, particularly wherein the target-binding moiety specifically binds to an epitope of epithelial cell adhesion molecule (EpCAM).

8. The conjugate of claim 1, wherein the target-binding moiety is selected from the group consisting of:

(i) antibody or antigen-binding fragment thereof;

(ii) antibody-like protein; and (iii) nucleic acid aptamer.

9. The conjugate of claim 8, wherein the antibody or the antigen-binding fragment thereof is selected from a diabody, a tetrabody, a nanobody, a chimeric antibody, a deimmunized antibody, a humanized antibody or a human antibody.

10. The conjugate of claim 8, wherein the antigen binding fragment is selected from the group consisting of Fab, F(ab')$_2$, Fd, Fv, single-chain Fv, and disulfide-linked Fvs (dsFv).

11. The conjugate of claim 1 for use as a medicament.

12. The conjugate of claim 1 for the treatment of cancer in a patient, wherein the cancer is selected from the group consisting of pancreatic cancer, cholangiocarcinoma, breast cancer, colorectal cancer, lung cancer, prostate cancer, ovarian cancer, stomach cancer, kidney cancer, malignant melanoma, leukemia, and malignant lymphoma.

13. Pharmaceutical composition comprising the conjugate according to claim 1 and further comprising one or more pharmaceutically acceptable diluents, carriers, excipients, fillers, binders, lubricants, glidants, disintegrants, adsorbents; and/or preservatives.

14. An amatoxin-conjugation molecule comprising a linker L connected to an amatoxin via (i) the γ C-atom of amatoxin amino acid 1, particularly via an amide linkage;

(ii) an oxygen atom bound to the δ C-atom of amatoxin amino acid 3, particularly via an ester linkage, an ether linkage or a urethane linkage; or (iii) the 6' C-atom of amatoxin amino acid 4, particularly via an oxygen atom bound to the 6' C-atom of amatoxin amino acid 4;

in each case wherein the linker L comprises a carbamic acid derivative —NH—C(O)—X, wherein X is a leaving group that can be replaced by a primary amine of a target-binding moiety.

15. The amatoxin-conjugation molecule claim 14, wherein X is selected from: $^{t}$butyloxy, -succinimidyloxy, -1-O-succinimidyloxy-3-sulfonate (-Sulfo-NHS), —O-(4-nitrophenyloxy), —O-(3-nitrophenyloxy), —O-(2,4-dinitrophenyloxy), —O-(2,4-dichloro-6-nitrophenyloxy), -pentafluorophenyloxy, -pentachlorophenyloxy, —O-(2,4,5-trichlorophenyloxy), —O-(3,4-dihydro-3-hydroxy-4-oxo-1,2,3-benzotriazine-3-yl), —O-(endo-1-hydroxy-5-norbornene-2,3-dicarboximide-1-yl), -1-phthalimidoyloxy, -1-benzotriazolyloxy, -1-(7-aza-benzotriazolyl)oxy, and —N-imidazolyl.

16. A method for synthesizing a conjugate of any one of claims 1 to 12, comprising the step of reacting an amatoxin-conjugation molecule of claim 14 or 15 with a target-binding moiety comprising a primary amino group.

* * * * *